(12) United States Patent
Compernolle et al.

(10) Patent No.: US 7,307,060 B2
(45) Date of Patent: Dec. 11, 2007

(54) HYPOXIA INDUCIBLE FACTOR 2α FOR CURING NEONATAL RESPIRATORY DISTRESS SYNDROME AND AS A TARGET FOR THE TREATMENT OF PULMONARY HYPERTENSION

(75) Inventors: Veerle Compernolle, Wilsele (BE); Peter Carmeliet, Blanden (BE)

(73) Assignee: Vlaams Interuniversitair Instituut voor Biotechnologie VZW, Zwinjnaarde (BE)

(*) Notice: Subject to any disclaimer, the term of this patent is extended or adjusted under 35 U.S.C. 154(b) by 0 days.

(21) Appl. No.: 11/226,771

(22) Filed: Sep. 14, 2005

(65) Prior Publication Data

US 2006/0205645 A1  Sep. 14, 2006

Related U.S. Application Data

(62) Division of application No. 10/475,403, filed as application No. PCT/EP02/04479 on Apr. 24, 2002, now abandoned.

(30) Foreign Application Priority Data

| Apr. 24, 2001 | (EP) | ................................. 01201481 |
| Aug. 10, 2001 | (EP) | ................................. 01203073 |
| Jan. 11, 2002 | (EP) | ................................. 02075077 |

(51) Int. Cl.
  *A61K 38/00* (2006.01)
(52) U.S. Cl. ......................................................... 514/2
(58) Field of Classification Search .................... None
  See application file for complete search history.

(56) References Cited

U.S. PATENT DOCUMENTS 5,695,963 A    12/1997  McKnight et al.
  5,840,693 A    11/1998  Eriksson et al.
  6,613,563 B1 *  9/2003  Sosnowski et al. ...... 435/320.1

OTHER PUBLICATIONS

Iassus et al., Vascular endothelial growth factor in human preterm lung, Am J Respir Crit Care Med., May 1999, vol. 159, pp. 1429-1433.*

Acarregu et al., Vascular endothelial growth factor gene expression in human fetal lung in vitro, Am J Respir Cell Mol Biol., Jan. 1999, vol. 20, No. 1, pp. 14-23.*

Maniscalco et al., Hyperoxic injury decreases alveolar epithelial cell expression of vascular endothelial growth factor (VEGF) in neonatal rabbit lung., Am J Respir Cell Mol Biol., May 1997, vol. 16, No. 5, pp. 557-567.*

Jaakkola, et al. "Targeting of HIF-α to the von Hippell-Lindau Ubiquitylation Complex by $O_2$-Regulated Prolyl Hydroxylation," *Science*, vol. 292, pp. 468-472, Apr. 20, 2001.

Peng, et al. "The Transcription Factor EPAS-1/Hypoxia-Inducible Factor 2α Plays an Important Role in Vascular Remodeling," *Proceedings of the National Academy of Sciences*, vol. 97, No. 15, pp. 8386-8391, Jul. 18, 2000.

Semenza, "HIF-1 and Human Disease: One Highly Involved Factor," *Genes & Development*, vol. 14, pp. 1983-1991, 2000.

Tian, et al. "Endothelial PAS Domain Protein 1 (EPAS1), a Transcription Factor Selectively Expressed in Endothelial Cells," *Genes & Development*, vol. 11, pp. 72-82, 1997.

International Search Report, issued Jul. 22, 2003.

Acarregui, et al. "Vascular Endothelial Growth Factor (VEGF) Induces Airway Epithelial Cell Proliferation and Surfactant Protein Gene Expression in Human Fetal Lung In Vitro," Abstract from Annual Meeting of the American Pediatric Society and The Society for Pediatric Research held in New Orleans, LA, May 1-5, 1998, p. 44A.

Creuwels, et al. "The Pulmonary Surfactant System: Biochemical and Clinical Aspects," *Lung* vol. 175, No. 1, pp. 1-39, 1997.

Ema, et al. "A Novel bHLH-PAS Factor with Close Sequence Similarity to Hypoxia-Inducible Factor 1-α Regulates the VEGF Expression and Its Potentially Involved in Lung and Vascular Development," *Proceedings of the National Academy of Sciences of USA*, vol. 94, pp. 4273-4278, Apr. 1997.

European Search Report dated Mar. 15, 2007.

* cited by examiner

*Primary Examiner*—Robert B. Mondesi
(74) *Attorney, Agent, or Firm*—Knobbe, Martens, Olson & Bear, LLP

(57) ABSTRACT

The current invention relates to the field of hypoxia-induced disorders and more specifically to the use of hypoxia inducible factor 2α as a target in a method for the screening for molecules that can be used for the treatment of pulmonary hypertension. The invention further relates to the use of HIF-2α and/or of the HIF-2α inducible protein VEGF for the treatment of neonatal respiratory distress syndrome.

5 Claims, 1 Drawing Sheet

Figure 1:
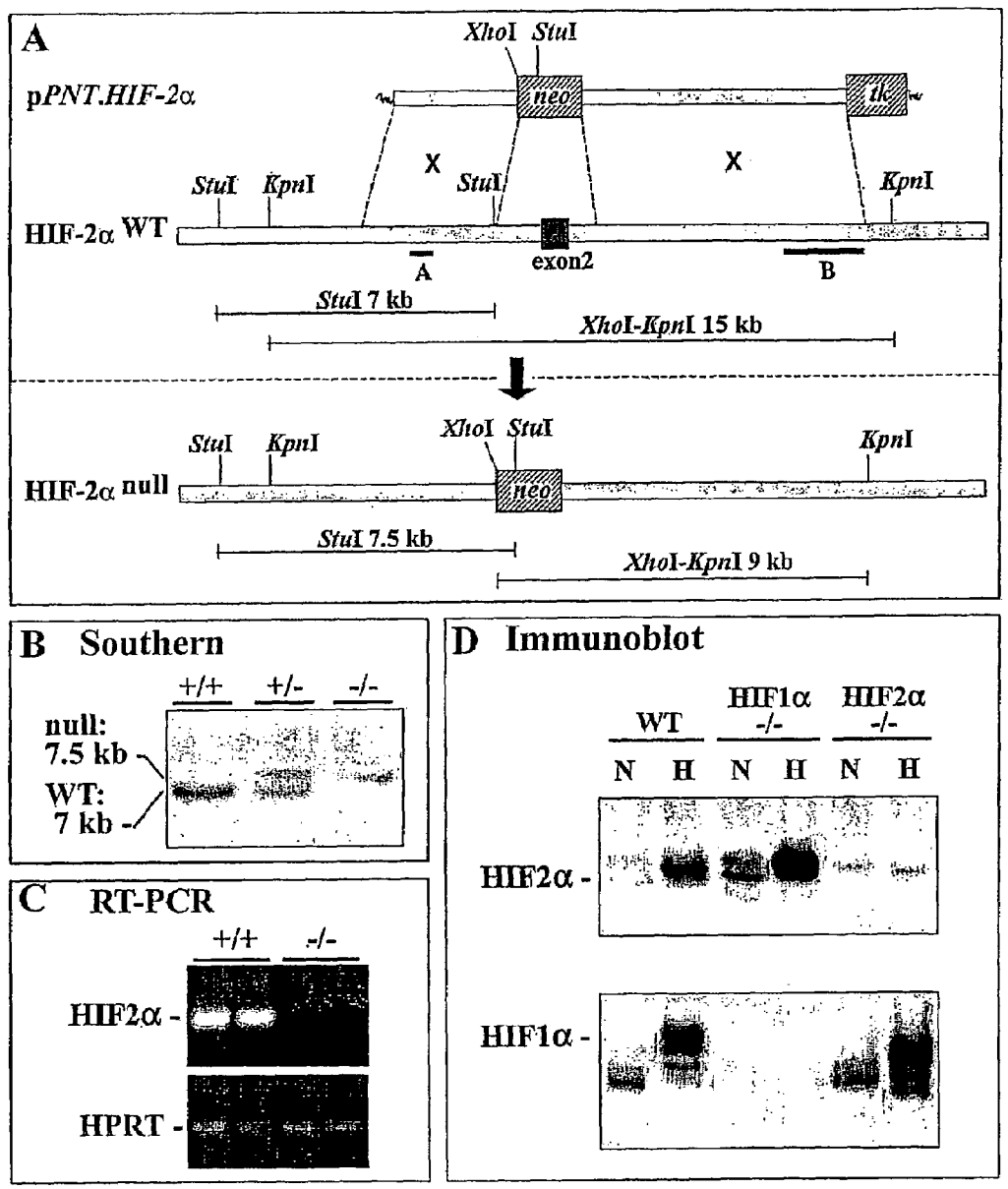

HYPOXIA INDUCIBLE FACTOR 2α FOR CURING NEONATAL RESPIRATORY DISTRESS SYNDROME AND AS A TARGET FOR THE TREATMENT OF PULMONARY HYPERTENSION

RELATED APPLICATIONS

This application is a divisional application of U.S. application Ser. No. 10/475,403, filed Jan. 12, 2004, now abandoned, which is the U.S. National Phase under 35 U.S.C. §371 of International Application PCT/EP02/04479, filed Apr. 24, 2002, which claims priority of EP 01201481.7, filed Apr. 24, 2001; EP 01203073.0, filed Aug. 10, 2001; and EP 02075077.4, filed Jan. 11, 2002.

FIELD OF THE INVENTION

The current invention relates to the field of hypoxia-induced disorders and more specifically to the use of hypoxia inducible factor 2α (HIF-2α) as a target in a method for the screening for molecules that can be used for the treatment of pulmonary hypertension. The invention further relates to the use of HIF-2α and/or the HIF-2α inducible protein VEGF for the treatment of neonatal respiratory distress syndrome.

BACKGROUND OF THE INVENTION

Preterm delivery is the chief problem in obstetrics today, affecting 10% of all births[1]. It accounts for more than 70% of perinatal mortality and nearly half of long-term neurological morbidity, especially in infants who are born at less than 32 weeks of gestation and weigh less than 1,000 g. With ~60% of these newborns developing respiratory distress syndrome (RDS) and a 50% lethality, RDS is the leading cause of neonatal mortality[2]. RDS results from insufficient production of surfactant by immature type 2 pneumocytes in preterm infants, but can also result from dysfunction or deficiency of surfactant in term infants due to inherited mutations, meconium aspiration, hemorrhage, infections and others[3]. Surfactant is a mixture of phospholipids and surfactant-associated proteins (SP-A to SP-D), which lowers surface tension at the air-water interface and thereby prevents alveolar collapse and respiratory failure. Surfactant phospholipids are synthetized from substrates, provided by glycogen stores in fetal immature pneumocytes[4]. Neonatal intensive care has improved the survival of infants with RDS, but often at the expense of the development of bronchopulmonary dysplasia or chronic lung disease of prematurity[5]. Treatment with oxygen may irreversibly damage lung parenchyma and angiogenesis, while prenatal steroid treatment causes neurological, metabolic, cardiovascular and hormonal side-effects, and impairs growth[6]. Surfactant treatment is effective, but expensive and only symptomatic[7].

Interactions between branching airways and blood vessels are critical for normal lung development[8]. A major factor in lung vascular development is vascular endothelial growth factor (VEGF), which binds its receptors Flk-1 (VEGF-R2) and Flt-1 (VEGF-R1)[9]. Three VEGF-isoforms exist: a diffusable $VEGF_{120}$, a matrix-bound $VEGF_{188}$ and $VEGF_{164}$, which can bind matrix and is still diffusable. VEGF is deposited at the leading edge of branching airways, where it stimulates vascularization[10]. Indirect evidence suggests, however, that VEGF also affects epithelial growth and differentiation. Type 2 pneumocytes and bronchiolar epithelial cell produce VEGF and possess VEGF receptors[11,12]. VEGF levels are also considerably higher in the broncho-alveolar fluid than in the blood[12], suggesting that epithelial cells affect their own function by releasing VEGF into the airway lumen. Remarkably, the lung is one of the few organs where VEGF levels remain elevated in the adult, even though no active angiogenesis occurs. Previous studies provided circumstantial evidence for a role of VEGF in lung development, but did not provide functional in vivo proof for a role of VEGF in lung maturation and surfactant production. For instance, VEGF levels in tracheal aspirate were lower in infants with lung immaturity developing bronchopulmonary dysplasia than in those surviving without pulmonary complications in some[13-15] but not in other studies[16]. Exogenous VEGF stimulates growth of epithelial cells in early embryonic lung explants in vitro[17], but the relevance of endogenous VEGF for lung maturation just prior to birth in vivo and the possible therapeutic potential of VEGF in preventing RDS in preterm infants remain unknown. In the present invention we show that loss of HIF-2α causes fatal RDS in newborn due to insufficient surfactant production. We show that VEGF plays an important role in lung maturation since VEGF levels are reduced in HIF-2α deficient mice, neonates expressing only the $VEGF_{120}$ isoform or with impaired HIF-2α-dependent VEGF expression die of RDS, and intra-amniotic administration of anti-Flk-1 antibodies aggravated lung prematurity. Importantly, intra-uterine delivery of VEGF before birth or intra-tracheal injection of VEGF after birth stimulates conversion of glycogen to surfactant, improved lung function and prevented RDS in premature. In summary, one aspect of the invention shows the use of VEGF for the manufacture of a medicament to treat RDS in premature infants.

A second aspect of the invention deals with the manufacture of a medicament to treat and/or to prevent pulmonary hypertension. Hypoxia causes proliferation of pulmonary vascular cells, in contrast with the usual growth-suppressive effect of hypoxia on most other cell types. Chronic hypoxic conditions are known to induce pulmonary vascular remodeling and subsequent pulmonary hypertension and right ventricular hypertrophy, thereby constituting a major cause of morbidity and mortality in patients with chronic obstructive pulmonary disease (COPD). Although several molecules such as endothelin-1 and platelet derived growth factor (PDGF) are believed to play an important role during pulmonary hypertension, the precise molecular mechanisms of this process are still elusive. It has been shown that the transcription factor HIF-1α is involved in the physiological response to chronic hypoxia. Heterozygous HIF-1α$^\pm$ mice showed delayed polycythemia and right ventricular hypertrophy and impaired pulmonary hypertension and vascular remodeling after exposure to chronic hypoxia, indicating a significant role for HIF-1α in the development of pulmonary hypertension. HIF-1α was originally cloned as a basic helix-loop-helix transcription factor, mediating the cellular adaptation to hypoxia. During hypoxia HIF-1α upregulates the expression of a number of genes involved in erythropoiesis, glycolysis and angiogenesis by formation of a heterodimer with HIF-1β (also termed aryl hydrocarbon receptor nuclear translocator; ARNT), which binds to a hypoxia-response element (HRE) in the promoter of these target genes. In addition, HIF-1α has also been implicated in the induction of apoptosis in hypoxic and hypoglycaemic conditions. Recently, a novel hypoxia-inducible factor, HIF-2α (also known as EPAS-1, HLF, HRF or MOP2) was identified, which is also able to bind to hypoxia-response elements after heterodimerization with HIF-1β. Although HIF-2α is a homologue of HIF-1α, the role of HIF-2α in glycolytic, angiogenic, apoptotic or possible disease processes is unknown and unpredictable. In the present invention, we have examined the endogenous role of HIF-2α by targeted gene-inactivation in murine embryonic stem (ES) cells. It has been found that HIF-2α is a new therapeutic target for the treatment of pulmonary hypertension.

FIGURE LEGEND

FIG. 1: Targeting of the HIF-2α gene.

(A) Top, targeting vector pPNT.HIF-2α; middle, map of the wild type (WT) gene; bottom, homologously recombined (HR) HIF-2α allele. Analytical restriction digests and hybridization probes A (0.6-kb NcoI-EcoRV fragment) and B (2.3-kb NheI-EcoRI fragment) for genotyping are indicated. (B) Southern blot analysis (probe A) of StuI-digested genomic DNA from ES cells generating a 7-kb WT and 7.5-kb HR HIF-2α allele. (C) RTPCR analysis of total RNA of ES cells for HIF-2α gene expression. HPRT gene expression was used as an internal control. (D) Immunoblot analysis on total cell extract from WT, HIF-1α$^{-/-}$ and HIF-2α$^{-/-}$ ES cells for HIF-2α gene expression during normoxia (N) and hypoxia (H).

Aims and Detailed Description of the Invention

One aspect of the present invention demonstrates that development of pulmonary vascular remodeling during chronic hypoxia is mediated by HIF-2α. Immunohistochemical analysis revealed that hypoxia induced a significant increase of vessel muscularization in the periphery of the lung (distal from the bronchi) in WT mice, as observed by the increase of vessels that were completely covered by smooth muscle cells or that contained both an internal and an external elastic lamina. However, under hypoxic conditions, HIF-2α$^{\pm}$ mice showed no vascular remodeling, since vessel muscularization was comparable to that in normoxic HIF-2α$^{\pm}$ mice and normoxic WT mice. A similar pattern was observed for the right ventricular blood pressure, which was markedly increased in WT mice, but not in HIF-2α$^{\pm}$ mice. These findings demonstrate that the respons to the reduction of environmental oxygen was completely abolished in HIF-2α$^{\pm}$ mice, since both normoxic WT mice, normoxic HIF-2α$^{\pm}$ mice and hypoxic HIF-2α$^{\pm}$ mice showed comparable values for the different parameters analyzed. In agreement with their pulmonary hypertension and vascular remodeling, WT mice also showed severe right ventricle hypertrophy. In contrast, no right ventricle hypertrophy was observed in HIF-2α$^{\pm}$ mice, in agreement with the absence of pulmonary hypertension. Exposure to chronic hypoxia for 8 weeks also failed to induce pulmonary hypertension and right ventricle hypertrophy in HIF-2α$^{\pm}$ mice, excluding that this pathology was only delayed in HIF-2α$^{\pm}$ mice. WT mice did not survive for 8 weeks under these conditions, and started dying after 4 weeks exposure to 10% O$_2$. Contrary to WT mice, HIF-2α$^{\pm}$ mice were protected against hypoxia-induced pulmonary hypertension, vascular remodeling and right ventricle hypertrophy. In the present invention we show that the right ventricular hypertrophy is surprisingly absent in the HIF-2α$^{\pm}$ mice. In the art it is shown that HIF-1α$^{\pm}$ mice lose weight than WT mice during chronic hypoxia, despite their reduced pulmonary hypertension. In contrast, here we observed that WT mice lost more weight than HIF-2α$^{\pm}$ mice in hypoxia, which is in agreement with the prevention of pulmonary hypertension in HIF-2α$^{\pm}$ mice. A loss of weight has also been observed in patients suffering chronic obstructive pulmonary disease. Possibly, since HIF-1α regulates expression of glucose metabolizing enzymes, HIF-1α may be involved in general metabolism and growth, thereby explaining the increased weight loss of hypoxic HIF-1α$^{\pm}$ mice. In contrast, this invention shows that despite the homology between HIF-2α and HIF-1α, that HIF-2α is only poorly involved in the regulation of glycolysis. Whereas HIF-1α$^{\pm}$ mice were found to be only partially protected against pulmonary hypertension, both pulmonary vascular remodeling, pulmonary hypertension and right ventricular hypertrophy were absent in HIF-2α$^{\pm}$ mice when exposed to chronic hypoxia. The fact that this phenotype was more pronounced in HIF-2α$^{\pm}$ mice than in HIF-1α$^{\pm}$ was an unexpected finding. Taken together, the present invention shows that HIF-2α plays, to our surprise, a more important role than HIF-1α in hypoxic lungs and hence the invention demonstrates a crucial role for HIF-2α in the development of pulmonary hypertension and vascular remodeling and implies the use of HIF-2α inhibitors to prevent hypoxia-induced pulmonary hypertension, a pathology with high morbidity and mortality.

Therefore, in a first embodiment the invention provides the use of the hypoxia inducible factor 2α (HIF-2α) or fragments thereof as a target in a method to screen for molecules that are able to inhibit the development of pulmonary hypertension wherein said method to screen for molecules comprises the following steps a) incubating a mixture comprising HIF-2α or a fragment thereof and at least one molecule, b) allowing binding between HIF-2α or a fragment thereof and said molecule, c) isolating said molecule binding to HIF-2α, or a fragment thereof and d) determining the ability of said molecule to inhibit the development of pulmonary hypertension.

More specifically, the invention is directed to molecules that act as antagonists of HIF-2α such as anti-HIF-2α antibodies and functional fragments derived thereof, antisense RNA and DNA molecules, ribozymes that function to inhibit the translation of HIF-2α, and a dominant negative form of HIF-2α all capable of interfering/or inhibiting the HIF-2α mediated transactivation. Small molecules can also interfere by binding on the promoter region of HIF-2α and inhibit binding of a transcription factor on said promoter region or said molecules can bind to HIF-2α itself and prevent binding of HIF-2α to a HIF-2α-responsive promoter.

The term 'antibody' or 'antibodies' relates to an antibody characterized as being specifically directed against HIF-2α or any functional derivative thereof, with said antibodies being preferably monoclonal antibodies; or an antigen-binding fragment thereof, of the F(ab')$_2$, F(ab) or single chain Fv type, or any type of recombinant antibody derived thereof. These antibodies of the invention, including specific polyclonal antisera prepared against HIF-2α or any functional derivative thereof, have no cross-reactivity to others proteins. The monoclonal antibodies of the invention can for instance be produced by any hybridoma liable to be formed according to classical methods from splenic cells of an animal, particularly of a mouse or rat immunized against HIF-2α or any functional derivative thereof, and of cells of a myeloma cell line, and to be selected by the ability of the hybridoma to produce the monoclonal antibodies recognizing HIF-2α or any functional derivative thereof which have been initially used for the immunization of the animals. The monoclonal antibodies according to this embodiment of the invention may be humanized versions of the mouse monoclonal antibodies made by means of recombinant DNA technology, departing from the mouse and/or human genomic DNA sequences coding for H and L chains or from cDNA clones coding for H and L chains. Alternatively the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also fragments derived from these monoclonal antibodies such as Fab, F(ab)'$_2$ and scFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type. In another embodiment of the invention the inhibitor of HIF-2α can be a camel antibody or a functional fragment thereof. Camel antibodies are fully described in WO94/25591, WO94/04678 and in WO97/49805. The camel antibody can be directed to HIF-2α, preventing the binding and/or subsequent signal transduction of HIF-2α. Antibodies can be used to hit intracellular targets such as HIF-2α by processes as for example 'antibody lipidation', the latter is fully described in WO94/01131.

Random peptide libraries consisting of all possible combinations of amino acids attached to a solid phase support may be used to identify peptides that are able to bind to the ligand binding site of a given receptor or other functional domains of a receptor such as kinase domains (Lam K S et al., 1991, Nature 354, 82). The screening of peptide libraries may also have therapeutic value in the discovery of pharmaceutical agents that act to inhibit the biological activity of HIF-2α. Identification of molecules that are able to bind to HIF-2α may be accomplished by for example screening a peptide library with recombinant soluble HIF-2α protein.

Also within the scope of the invention are oligoribonucleotide sequences, that include anti-sense RNA and DNA molecules and ribozymes that function to inhibit the translation of HIF-2α mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the HIF-2α nucleotide sequence, are preferred. Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of HIF-2α RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines.

The invention also provides methods for identifying molecules that bind on HIF-2α and antagonize the signal transduction. These methods are also referred to as 'drug screening assays' or 'bioassays' and typically include the step of screening a candidate/test compound or agent for the ability to interact with HIF-2α. Candidate compounds or agents, which have this ability, can be used as drugs to combat or prevent pulmonary hypertension. Candidate/test compounds such as small molecules, e.g. small organic molecules, and other drug candidates can be obtained, for example, from combinatorial and natural product libraries as described above. As a non-limited example the assays are cell-free assays which include the steps of combining HIF-2α and a candidate/test compound, e.g., under conditions which allow for interaction of (e.g. binding of) the candidate/test compound with HIF-2α to form a complex, and detecting the formation of a complex, in which the ability of the candidate compound to interact with HIF-2α is indicated by the presence of the candidate compound in the complex. Formation of complexes between the HIF-2α and the candidate compound can be quantitated, for example, using standard immunoassays. The HIF-2α employed in such a test may be free in solution, affixed to a solid support, borne on a cell surface, or located intracellularly. To perform the above described drug screening assays, it is feasible to immobilize HIF-2α or its (their) target molecule(s) to facilitate separation of complexes from uncomplexed forms of one or both of the proteins, as well as to accommodate automation of the assay. Interaction (e.g., binding of) of HIF-2α to a target molecule, can be accomplished in any vessel suitable for containing the reactants. Examples of such vessels include microtiter plates, test tubes, and microcentrifuge tubes. In one embodiment, a fusion protein can be provided which adds a domain that allows the protein to be bound to a matrix. For example, HIF-2α tagged can be adsorbed onto Ni-NTA microtiter plates, or HIF-2α-ProtA fusions adsorbed to IgG, which are then combined with the cell lysates (e.g., $^{35}$S-labeled) and the candidate compound, and the mixture incubated under conditions conducive to complex formation (e.g., at physiological conditions for salt and pH). Following incubation, the plates are washed to remove any unbound label, and the matrix immobilized and radiolabel determined directly, or in the supernatant after the complexes are dissociated. Alternatively, the complexes can be dissociated from the matrix, separated by SDS-PAGE, and the level of HIF-2α binding protein found in the bead fraction quantitated from the gel using standard electrophoretic techniques. Other techniques for immobilizing protein on matrices can also be used in the drug screening assays of the invention. For example, either HIF-2α or its target molecules can be immobilized utilizing conjugation of biotin and streptavidin. Biotinylated HIF-2α can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HIF-2α but which do not interfere with binding of the protein to its target molecule can be derivatized to the wells of the plate, and HIF-2α trapped in the wells by antibody conjugation. As described above, preparations of a HIF-2α-binding protein and a candidate compound are incubated in the HIF-2α-presenting wells of the plate, and the amount of complex trapped in the well can be quantitated. Methods for detecting such complexes, in addition to those described above for the GST-immobilized complexes, include immunodetection of complexes using antibodies reactive with the HIF-2α-target molecule, or which are reactive with HIF-2α and compete with the target molecule; as well as enzyme-linked assays which rely on detecting an enzymatic activity associated with the target molecule. Another technique for drug screening which provides for high throughput screening of compounds having suitable binding affinity to HIF-2α is described in detail in "Determination of Amino Acid Sequence Antigenicity" by Geysen H N, WO 84/03564, published on Sep. 09, 1984. In summary, large numbers of different small peptide test compounds are synthesized on a solid substrate, such as plastic pins or some other surface. The protein test compounds are reacted with fragments of HIF-2α a nd washed. Bound HIF-2α is then detected by methods well known in the art. Purified HIF-2α can also be coated directly onto plates for use in the aforementioned drug screening techniques. Alternatively, non-neutralizing antibodies can be used to capture the peptide and immobilize it on a solid support. This invention also contemplates the use of competitive drug screening assays in which neutralizing antibodies capable of binding HIF-2α specifically compete with a test compound for binding HIF-2α. In this manner, the antibodies can be used to detect the presence of any protein, which shares one or more antigenic determinants with HIF-2α.

In a further embodiment the invention provides the use of HIF-2α or fragments thereof in a method to screen for molecules that are able to inhibit the development of pulmonary hypertension wherein said method comprises the following steps: a) incubating a mixture comprising HIF-2α or a fragment thereof, a reporter construct wherein the reporter gene is driven by the transcription factor HIF-2α, and at least one molecule, b) determining if the latter incubation results in at least 50% reduction in expression of said reporter gene, and c) determining the ability of said molecule to inhibit the development of pulmonary hypertension.

It is expected that a molecule able to reduce the expression of a reporter gene by at least 30%, 40%, 50%, 60%, 70%, 80%, 90% or 100% will also reduce the level of HIF-2α protein when said molecule is applied to a cell culture or an organism. Since the HIF-2α$^\pm$ mice are protected against pulmonary hypertension, at least 50% reduction or inhibition of its activity of HIF-2α protein might be necessary and sufficient to inhibit pulmonary hypertension.

By molecules it is meant peptides, proteins, organic molecules and carbohydrates. Small molecules, eg small organic molecules, and other drug candidates can be obtained, for example, from combinatorial and natural product libraries. Random peptide libraries consisting of all possible combinations of amino acids attached to a solid phase support may also be used to identify peptides that are able to bind to specific ligands (Lam K S et al., 1991, Nature 354, 82).

A "reporter gene" is a DNA molecule that expresses a detectable gene product, which may be RNA or protein. The detection may be accomplished by any method known to one of skill in the art. For example, detection of mRNA expression may be accomplished by using Northern blots and detection of protein may be accomplished by staining with antibodies specific to the protein. Preferred reporter genes are those that are readily detectable. A reporter gene may be operably linked in a DNA construct with a regulatory DNA sequence such that detection of the reporter gene product provides a measure of the transcriptional activity of the regulatory sequence. Examples of reporter genes include, but are not limited to, those coding for chloramphenicol acetyl transferase (CAT), luciferase, beta-galactosidase and alkaline phosphatase. The term "operably linked" refers to linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease respectively the transcription of the DNA sequence. Enhancers and silencers may be located upstream, downstream or embedded within the coding regions of the DNA sequence. A DNA for a signal sequence is operably linked to DNA coding for a polypeptide if it is expressed as a pre-protein that participates in the secretion of the polypeptide. Linkage of DNA sequences to regulatory sequences is typically accomplished by ligation at suitable restriction sites or adapters or linkers inserted in lieu thereof using restriction endonucleases known to one of skill in the art.

A promoter construct operably linked to for example a reporter gene may be transfected into a cell line using any technique previously described to produce for example a stable cell line, but also transiently transfected host cells can be used, containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed and subsequently analysed. The level of expression in the presence of the test compound may be compared with the level of expression in the absence of the test compound.

"Pulmonary hypertension" is a specific condition of hypertension in the lung and relates to arterial hypertension, capillary hypertension or venous-hypertension in the lung. Suitably, the term "pulmonary hypertension" relates to pulmonary arterial hypertension.

Furthermore it will be understood that pulmonary arterial hypertension relates to—but is not restricted to—both primary arterial hypertension and to pulmonary arterial hypertension occurring secondary to pulmonary diseases such as chronic bronchitis, emphysema, kyphoscoliosis and conditions such as chronic mountain sickness. Pulmonary hypertension is a serious medical condition that may lead to right ventricular hypertrophy, failure and death. When used herein the term "right heart failure" relates to disorders such as cor pulmonale and congenital abnormalities of the heart. It will be appreciated that cor pulmonale often occurs secondary to certain lung diseases such as chronic bronchitis and emphysema. Congenital abnormalities of the heart include disorders, such as atrial septal defect, tetralogy of fallot, venticular septal defect and persistent ductus arteriosus.

In another embodiment the invention provides a method for the production of a pharmaceutical composition comprising the usage of HIF-2α or a fragment thereof in a method to screen for molecules that are able to inhibit the development of pulmonary hypertension and further more mixing said molecule identified, or a derivative or homologue thereof, with a pharmaceutically acceptable carrier.

In a second aspect of the invention evidence is provided yet another embodiment the invention provides in vivo evidence that HIF-2α and its downstream target VEGF are critical for fetal lung maturation. Loss of HIF-2α, absence of critical VEGF isoforms or inhibition of VEGF in utero all impaired lung maturation and caused RDS at birth due to insufficient surfactant production. We show that when VEGF is administered intra-amniotically to unborn fetuses or intra-tracheally after birth, it increases conversion of glycogen stores to surfactant, improves lung function, protects severely preterm mice against RDS and prolongs their survival, with a comparable efficiency as prenatal steroid treatment but without acute adverse effects. Thus, the present invention demonstrates an important role for VEGF for the treatment of respiratory distress syndrome.

In another embodiment the invention provides the use of HIF-2α or a fragment or homologue thereof for the manufacture of a medicament to treat neonatal respiratory distress syndrome.

In another embodiment the invention provides the use of VEGF or a fragment or homologue thereof, that is induced by HIF-2α, for the manufacture of a medicament to treat neonatal respiratory distress syndrome.

In a particular embodiment the invention provides the use of $VEGF_{165}$ for the manufacture of a medicament to treat neonatal respiratory distress syndrome.

The term 'medicament to treat' relates to a composition comprising molecules as described above and a pharmaceutically acceptable carrier or excipient (both terms can be used interchangeably) to treat diseases as indicated above (pulmonary hypertension and respiratory distress syndrome). The administration of a compound or a pharmaceutically acceptable salt thereof may be by way of oral, inhaled or parenteral administration. In a preferred embodiment inhaled administration is preferred. The active compound may be administered alone or preferably formulated as a pharmaceutical composition. An amount effective to treat the disorders hereinbefore described depends on the usual factors such as the nature and severity of the disorders being treated and the weight of the mammal. However, a unit dose will normally contain 0.01 to 50 mg for example 0.01 to 10 mg, or 0.05 to 2 mg of the identified compound or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. In a particular embodiment the compound (e.g. $VEGF_{165}$) or a pharmaceutically acceptable salt thereof is administered in an intra-uterine way (or intra-amniotically). In another particular embodiment the compound (e.g. $VEGF_{165}$) or a pharmaceutically acceptable salt thereof is administered intra-tracheally. Such compositions are prepared by admixture and are suitably adapted for oral, inhaled, intra-amniotic, intra-tracheal or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example between 1 and 5 microns, such as between 2 and 5 microns. A favored inhaled dose will be in the range of 0.05 to 2 mg, for example 0.05 to 0.5 mg, 0.1 to 1 mg or 0.5 to 2 mg. For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound. Where appropriate, small amounts of bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

The present invention further provides a pharmaceutical composition for use in the treatment and/or prophylaxis of herein described disorders which comprises a molecule or a pharmaceutically acceptable salt thereof, or a pharmaceutically acceptable solvate thereof, and, if required, a pharmaceutically acceptable carrier thereof. Another pharmaceutically acceptable composition is an inhalation composition, suitably in unit dosage form. Such compositions may be prepared in the manner as hereinbefore described.

In yet another embodiment genetic constructs operably linked to HIF-2α or to functional fragments thereof or genetic constructs operably linked to VEGF or homologues or fragments thereof can also be used to manufacture a medicament. One possibility is the use in gene therapy. A 'genetic construct' means any genetic element, coding or non-coding or anti-sense genetic information. Gene therapy means the treatment by the delivery of therapeutic nucleic acids to patient's cells. This is extensively reviewed in Lever and Goodfellow 1995; *Br. Med Bull.*, 51, 1-242; Culver 1995; Ledley, F. D. 1995. *Hum. Gene Ther* 6, 1129. To achieve gene therapy there must be a method of delivering genes to the patient's cells and additional methods to ensure the effective production of any therapeutic genes. There are two general approaches to achieve gene delivery; these are non-viral delivery and virus-mediated gene delivery. As an example, but not limited to this, is the use of a virus-mediated gene delivery system with replication defective retroviruses to stably introduce genes into patient's cells.

In addition compounds are known that inhibit the ubiquitin-proteasome-dependent degradation of hypoxia-inducible factor proteins. An example is PR39 (Li et al (2000) *Nat Med*. 6(1): 49-55) which is a highly basic arginine/proline-rich peptide originally isolated from porcine intestine on the basis of its antibacterial activity. PR39 which is predominantly produced by blood-derived macrophages, is found at the sites of active inflammation, including skin wounds and myocardial infarction. In addition PR39 can rapidly cross cell membranes. The active sequence of PR39 is located in the first 11 amino acids. PR-11 is a truncated form of PR-39, composed of these 11 amino acids ($NH_2$-Arg-Arg-Arg-Pro-Arg-Pro-Pro-Tyr-Leu-Pro-Arg-COOH) (SEQ ID NO: 5). In a specific embodiment PR-11 is used for the manufacture of a medicament to treat respiratory distress syndrome. In another specific embodiment PR-11 is administrated to fetus by intra-amniotic (in utero) or to preterms by intra-tracheal injection.

The present invention has potential medical implications. Intra-amniotic or intra-tracheal delivery of VEGF improves surfactant production and protects preterm newborns against RDS. The rapidity with which VEGF stimulates conversion of preformed glycogen to surfactant phospholipids <5 hours) makes VEGF an attractive therapeutic target. VEGF did not cause adverse effects on vascular leakage or bleeding in the lung, possibly because it barely crossed the alveolar epithelium. Third, steroids are often used to induce lung maturation but may cause serious adverse effects[6]. The invention indicates that dexamethasone upregulates pulmonary VEGF expression in fetuses at low doses, but suppresses VEGF production at a high dose. Thus, excessive amounts of glucocorticoids can counteract the beneficial pneumotrophic effect of VEGF. Fourth, oxygen improves oxygenation of preterm infants with RDS but, since it also suppresses VEGF expression in alveolar type 2 pneumocytes[11], it would deprive alveolar cells from pneumotrophic effects. At the flip side of the coin, VEGF supplements can lower the toxicity of high oxygen concentrations in the neonate, as supported by indirect evidence that the protective effect of IL-13 against hyperoxic lung damage is mediated by VEGF[50]. In concert, the present invention shows that the pneumotrophic effect of VEGF has a therapeutic potential for lung maturation in preterm infants at risk for RDS.

EXAMPLES

1. Targeting of the HIF-2α Gene in ES Cells

A genomic BAC clone containing the murine HIF-2α gene sequences was obtained from Research Genetics, Inc. (Huntsville, Ala., USA). The region 8 kb upstream and 10 kb downstream of exon 2 was mapped using restriction digests and Southern blot analysis (FIG. 1). A 2-kb NheI/BamHI fragment and an immediately upstream 5-kb BamHI/EcoRI fragment containing the genomic sequence 3' to exon 2 were inserted via a three part ligation in the XbaI/EcoRI site of the pPNT vector, resulting in pPNT3'. The pPNT vector contained the neomycin phosphotransferase (neo) gene as positive selection marker and the thymidine kinase (TK) gene as negative selection marker. A 3.5-kb HindIII/StuI fragment containing the genomic sequence 5' to exon 2 was initially subcloned in pBluescript and afterwards inserted in the NotI/XhoI site of pPNT3'. The resulting construct (FIG. 1) was linearized by NotI and electroporated into R1 ES cells. Targeted inactivation of a single HIF-2α allele (HIF-2α$^\pm$) in ES cells was accomplished by homologous deletion of the second exon, encoding the basic helix-loop-helix (bHLH) domain, which is essential for DNA binding and dimerization of HIF-2α with ARNT to form a functional HIF-2-complex (FIG. 1).

After selection with G418 and Gancyclovir, ES clones were screened by Southern blot analysis (probe A) for the presence of an additional 7.5-kb StuI band (homologous recombinant) besides the wild type 7-kb fragment (FIG. 1). Positive ES clones were also screened with a second restriction digest (KpnI+XhoI, probe B) to confirm that homozygous recombination occurred correctly at both flanks. 22 positive homologous recombinant HIF-2α$^\pm$ ES clones were obtained out of a total of 75 screened ES clones. HIF-2α$^{-/-}$ ES cells with two inactivated HIF-2α alleles were obtained by selection of heterozygous HIF-2α$^\pm$ ES cells on high G418 (1.8 mg/ml). ES cell clones with a randomly integrated HIF-2α gene targeting vector and with two functional HIF-2α alleles (HIF-2α$^{+/+}$) were used as controls (further referred to as wild type; WT). Inactivation of the HIF-2α gene was confirmed by reverse transcriptase polymerase chain reaction (RT-PCR) and immunoblot analysis (FIG. 1).

2. Generation of HIF-2α Deficient Mouse Embryos

To generate HIF-2α deficient mice, heterozygous HIF-2α± ES clones were aggregated with diploid embryos and reimplanted in pseudo-pregnant recipient mice. High percentage chimaeras were selected from the offspring of these recipient mothers and crossed with wild types mice. When germline transmission occurred, heterozygous HIF-2α± mice were born from these matings. Offspring from inter-crossings of HIF-2α± mice contained only wild types and heterozygotes, but no homozygous HIF-2α$^{-/-}$ mice, indicating that deficiency of HIF-2α causes lethality in the embryonic stage. When embryos were collected at embryonic day E9.5, E10.5, E11.5 or E12.5 from pregnant HIF-2α± mothers, that were crossed with HIF-2α± males, Mendelian inheritance was confirmed (approximately 25% HIF-2α$^{-/-}$ embryos, 50% HIF-2α± embryos and 25% wild type embryos). However, beginning from E13.5, part of the homozygous HIF-2α$^{-/-}$ embryos started showing abnormalities. At E15.5, half of the HIF-2α$^{-/-}$ embryos was necrotic while the other 50% appeared normal. At E18.5 or immediately after birth (postnatal day p0), only half of the expected amount of homozygotes was observed (ratio WT: heterozygote: homozygote was approximately 2:4:1), whereas 1 day after birth (p1) litters contained only heterozygous and WT embryos. This indicates that 50% of the HIF-2α$^{-/-}$ embryos died around E14.5 while the other 50% died immediately after birth (within the first hours). Occasionaly, a HIF-2α$^{-/-}$ embryo was born alive and survived for 3-5 weeks, although this was a very small minority (less than 1% of the HIF-2α$^{-/-}$ embryos). These HIF-2α$^{-/-}$ mice were significantly smaller than WT and HIF-2α± littermates (50% weight reduction) and died after a few weeks.

3. Weight Analysis and Hematocrit Measurements 8 weeks old female VWT and HIF-2α± mice of comparable weights were placed in a sealed chamber under normobaric hypoxic conditions (10% $O_2$), while the control mice were kept in normal air (20% $O_2$). After 4 weeks, WT mice in normoxia showed more weight gain than HIF-2α± mice (5.6±0.8 g for WT mice versus 2.6±0.7 g for HIF-2α± mice, p=0.017 by t-test, n is 6 to 8), indicating that inactivation of a single HIF-2α allele already affects normal growth (Table 1). In contrast, after 4 weeks of hypoxia, WT mice lost more weight than HIF-2α± mice (7.8±0.5 g for WT mice versus 4.0±0.4 g, for HIF-2α± mice, p<0.001 by t-test, n is 17 to 19) (table 1). These data suggest that the WT mice suffered more stress than HIF-2α± mice, which resulted in more weight loss.

TABLE 1

Female 8 weeks old WT and HIF-2α$^{+/-}$ mice of comparable weights were kept under normoxia (N: 20% O2) or hypoxia (H: 10% O2) for 4 weeks. Weight gain analysis revealed that WT mice grew faster than HIF-2α$^{+/-}$ mice under normoxic conditions. However, after 4 weeks of hypoxia WT mice lost significantly more weight than HIF-2α$^{+/-}$ mice.

|  | Normoxia | | Hypoxia | |
| --- | --- | --- | --- | --- |
|  | WT | HIF-2α$^{+/-}$ | WT | HIF-2α$^{+/-}$ |
| Initial weight (g) | 26.3 ± 0.9 | 26.0 ± 0.9 | 26.5 ± 0.7 | 24.7 ± 0.6 |
| Final weight (g) | 31.9 ± 1.0 | 28.6 ± 1.0* | 18.9 ± 0.6 | 20.7 ± 0.5 |
| Weight gain (g) | 5.6 ± 0.8 | 2.6 ± 0.7* | −7.8 ± 0.5 | −4.0 ± 0.4* |

The data represent weight gain (g) ± SEM (n is 6 to 14).
*Statistically significant (P < 0.05) versus control (WT).

TABLE 2

Hematocrit and hemoglobin content of WT and HIF-2α$^{+/-}$ mice.

|  | Normoxia | | Hypoxia | |
| --- | --- | --- | --- | --- |
|  | WT | HIF-2α$^{+/-}$ | WT | HIF-2α$^{+/-}$ |
| Hematocrit (%) | 36.0 ± 1.0 | 33.7 ± 1.3 | 45.6 ± 1.4° | 46.3 ± 0.8° |
| Hemoglobin (g/dl) | 13.1 ± 0.4 | 11.7 ± 0.4* | 15.7 ± 0.4° | 16.0 ± 0.2° |

The data represent means ± SEM (n is 5 to 16).
°Statistically significant (P < 0.05) versus normoxia.
*Statistically significant (P < 0.05) versus WT.

In normoxic conditions, hematocrit levels were comparable in WT and HIF-2α± (mice (Table 2). Normoxic HIF-2α± mice showed slightly lower hemoglobin contents in their blood than WT mice (13.1±0.4 g/dl for WT mice versus 11.7±0.4 g/dl for HIF-2α± mice, p=0.035 by t-test, n is 5 to 7), however this small difference is unlikely to have caused any physiological alterations. After 4 weeks of hypoxia, hematocrit and hemoglobin content were increased in both WT mice and HIF-2α± mice, but values were comparable between the both genotypes, suggesting that HIF-2α is minimally involved in regulation of erythropoiesis (Table 2).

4. HIF-2α± Mice Show Impaired Pulmonary Vascular Remodeling During Chronic Hypoxia Staining for elastin on lung sections of normoxic WT and HIF-2α± mice revealed comparable densities of arterioles containing only an internal elastic lamina (IEL) or an IEL plus an incomplete external elastic lamina (EEL). Lungs of WT mice, maintained in hypoxic conditions for 4 weeks, showed a significant increase in thick-walled arterioles containing both an IEL and a complete EEL. In contrast, no vascular remodeling was observed in hypoxic HIF-2α± mice, in which the fraction of arterioles containing both an IEL and a complete EEL was comparable with that of normoxic WT and HIF-2α± mice (Table 3), indicating that heterozygous deficiency of HIF-2α completely abolished the hypoxic response in the development of pulmonary vascular remodeling.

TABLE 3

Hypoxia-induced pulmonary vascular remodeling: presence of elastic laminae.

|  | Normoxia | | Hypoxia | |
| --- | --- | --- | --- | --- |
|  | WT | HIF-2α$^{+/-}$ | WT | HIF-2α$^{+/-}$ |
| Single IEL | 1.87 ± 0.09 | 2.01 ± 0.11 | 0.98 ± 0.06° | 1.88 ± 0.07* |
| IEL + incomplete EEL | 0.98 ± 0.06 | 1.00 ± 0.04 | 1.13 ± 0.06 | 0.88 ± 0.09* |
| IEL + complete EEL | 0.19 ± 0.03 | 0.15 ± 0.01 | 0.73 ± 0.11° | 0.17 ± 0.02* |
| total | 2.99 ± 0.06 | 3.16 ± 0.14 | 2.84 ± 0.16 | 2.94 ± 0.13 |

The data represent means ± SEM (n = 6) of number of vessels per 100 alveoli containing a single internal elastic lamina (IEL) (non-muscularized), an IEL and an incomplete external elastic lamina (EEL) (partially muscularized), or an IEL and a complete EEL (fully muscularized). Last row represents the total amount of vessels surrounded by elastic laminae.
°Statistically significant (P < 0.05) versus normoxia.
*Statistically significant (P < 0.05) versus WT.

The differences in vascular remodeling between WT and HIF-2α± mice were confirmed by stainings for smooth muscle cell α-actin on lung sections. In comparison with HIF-2α± mice, lungs of WT mice contained significantly more fully muscularized arterioles that were completely surrounded by smooth muscle cells after hypoxic exposure. In HIF-2α± mice, most of the arterioles were only partially surrounded by smooth muscle cells after hypoxia (Table 4). Vessels that were not muscularized (not surrounded by smooth muscle cells) could not be visualized by smooth muscle cell α-actin staining.

TABLE 4

Hypoxia-induced pulmonary vascular remodeling: coverage by smooth muscle cells.

|  | Normoxia | | Hypoxia | |
| --- | --- | --- | --- | --- |
|  | WT | HIF-2α+/− | WT | HIF-2α+/− |
| Partial SMC coverage | 1.32 ± 0.05 | 1.27 ± 0.10 | 1.23 ± 0.10 | 1.21 ± 0.04 |
| Complete SMC coverage | 0.65 ± 0.06 | 0.60 ± 0.12 | 1.43 ± 0.09* | 0.66 ± 0.02 |

The data represent means ± SEM (n = 6) of number of vessels per 100 alveoli partially covered by smooth muscle cells (partially muscularized), or completely covered by smooth muscle cells (fully muscularized).
*Statistically significant (P < 0.05) versus control (WT/Normoxia).

5. HIF-2α± Mice Show Impaired Pulmonary Hypertension During Chronic Hypoxia

Hemodynamic measurements were performed to determine whether the decreased pulmonary vascular remodeling in HIF-2α± mice in hypoxia was associated with reduced pulmonary hypertension. Chronic hypoxia (4 weeks) caused a significant increase of the mean and the systolic blood pressure in the right ventricle (RV) of WT mice (Table 5). However, HIF-2α± mice showed comparable right ventricular blood pressures in normoxia and hypoxia, which were also comparable with pressures observed in normoxic WT mice. In normoxia, mean right ventricular pressures were 11.8±0.8 mm Hg for WT mice versus 10.9±0.7 mm Hg for HIF-2α± mice (p=NS, n is 6 to 7); in hypoxia mean pressures were 22.6±1.3 mm Hg for WT mice versus 11.8±0.9 mm Hg for HIF-2α± mice (p<0.001 by t-test, n is 4 to 5). Systolic right ventricular pressures in normoxia were 20.9±1.3 mm Hg for WT mice versus 20.8±1.0 mm Hg for HIF-2α± mice (p=NS, n is 6 to 7); in hypoxia systolic pressures were 40.8±1.5 mm Hg for WT mice versus 23.6±1.3 mm Hg for HIF-2α± mice (p<0.001 by t-test, n is 4 to 5) (Table 5). Heart beating frequencies were comparable in WT and HIF-2α± mice under both normoxic and hypoxic conditions. Although heart beating was slightly decreased in normoxic HIF-2α± mice when compared with normoxic WT mice (561±12 beats/min for WT mice versus 507±20 beats/min for HIF-2α± mice, p=0.04 by t-test, n=7), this difference was very small and unlikely to cause any physiological alterations. After hypoxic exposure, no differences were observed in the heart rates (519±21 beats/min for WT mice versus 537±30 beats/min for HIF-2α± mice, p=NS by t-test, n is 4 to 7).

Prolonged exposure to 10% $O_2$ (8 weeks) also failed to induce pulmonary hypertension in HIF-2α± mice, whereas WT mice did not survive for 8 weeks under these conditions. After 8 weeks of hypoxia, the mean right ventricular pressure was 12.9±1.1 mm Hg for HIF-2α± mice (versus 22.6±1.3 mm Hg for WT mice after 4 weeks hypoxia (p=0.004, n=4)); the systolic right ventricular pressure was 25.5±1.2 mm Hg for HIF-2α± mice after 8 weeks hypoxia (versus 40.8±1.5 mm Hg for WT mice after 4 weeks hypoxia (p<0.001 by t-test, n=4). Heart rate was slightly decreased in HIF-2α± mice after 8 weeks hypoxia (413±38 beats/min after 8 weeks hypoxia versus 507±20 beats/min in normoxia, p=0.05 by t-test, n is 5 to 7). Since right ventricular pressure was only increased in hypoxic WT mice but not in hypoxic HIF-2α± mice, these data indicate that heterozygous deficiency of HIF-2α protects mice against hypoxia-induced pulmonary hypertension.

TABLE 5

Systolic (A) and mean (B) right ventricular blood pressures were measured in WT and HIF-2α+/− mice under normoxia (N: 20% O2) or after hypoxic exposure (H: 10% O2) for 4 weeks. Hemodynamic analysis revealed no differences in right ventricular pressures under normoxia, however, WT mice showed increased right ventricular pressures under hypoxia, but HIF-2α+/− mice did not.

|  | Normoxia | | Hypoxia | |
| --- | --- | --- | --- | --- |
|  | WT | HIF-2α+/− | WT | HIF-2α+/− |
| Mean RV pressure | 11.8 ± 0.8 | 10.9 ± 0.7 | 22.6 ± 1.3* | 11.8 ± 0.9 |
| Systolic RV pressure | 20.9 ± 1.3 | 20.8 ± 1.0 | 40.8 ± 1.5* | 23.6 ± 1.3 |

The data represent pressures (mm Hg) ± SEM (n is 4 to 7).
*Statistically significant (P < 0.05) versus control (WT/Normoxia).

6. HIF-2α± Mice Show Impaired Right Ventricle Hypertrophy During Chronic Hypoxia Under normoxic conditions, no differences were observed between WT and HIF-2α± mice with respect to the ratio of the mass of the right ventricle (RV) to the mass of the left ventricle plus septum (LV+S) (0.33±0.02 for WT mice versus 0.31±0.03 for HIF-2α± mice, p=NS, n is 7 to 10). However, exposure for 4 weeks to hypoxic conditions significantly increased the ratio (RV)/(LV+S) in WT mice but not in HIF-2α± mice (0.55±0.06 for WT mice versus 0.31±0.03 for HIF-2α± mice, p=0.005 by t-test, n=6) (Table 6). Another index for measuring right ventricle hypertrophy is the ratio of the RV mass to the total body weight (W). Whereas no differences were observed under normoxic conditions (0.25±0.02 mg/g for WT mice versus 0.24±0.01 mg/g for HIF-2α± mice, p=NS, n is 7 to 10), in hypoxia the RV/W ratio was 1.6 fold increased in WT mice compared with HIF-2α± mice (0.44±0.03 mg/g for WT mice versus 0.27±0.02 mg/g for HIF-2α± mice, p=0.001 by t-test, n=6) (Table 6). Prolonged exposure to hypoxia (8 weeks) also failed to induce right ventricle hypertrophy in HIF-2α± mice, in agreement with the right ventricular blood pressure measurements. The ratio (RV)/(LV+S) was 0.28±0.04 in HIF-2α± mice after 8 weeks hypoxia (versus 0.55±0.06 in WT mice after 4 weeks hypoxia (p=0.01, n is 4 to 6)). The ratio RV/W was 0.29±0.03 mg/g in HIF-2α± mice after 8 weeks hypoxia (versus 0.44±0.03 mg/g in WT mice after 4 weeks hypoxia (p=0.01, n is 4 to 6)). No significant differences were observed between normoxic WT mice and hypoxic HIF-2α± mice, indicating that HIF-2α± mice are protected against hypoxia-induced right ventricle hypertrophy, which is in agreement with the impaired pulmonary hypertension and vascular remodeling in HIF-2α± mice during hypoxia.

TABLE 6

Right ventricular hypertrophy measurements in WT and HIF-2α$^{+/-}$ mice revealed no differences under normoxic conditions. However, after hypoxic exposure (4 weeks) the ratio of the mass of the right ventricle to the mass of the left ventricle plus septum (RV/LV + S) (A) and the ratio of the mass of the right ventricle to the total body weight (RV/W) (mg/g) (B) were increased in WT mice but not in HIF-2α$^{+/-}$ mice.

|  | Normoxia | | Hypoxia | |
| --- | --- | --- | --- | --- |
|  | WT | HIF-2α$^{+/-}$ | WT | HIF-2α$^{+/-}$ |
| RV/LV + S | 0.33 ± 0.02 | 0.31 ± 0.02 | 0.55 ± 0.06* | 0.31 ± 0.03 |
| RV/W (mg/g) | 0.25 ± 0.02 | 0.24 ± 0.02 | 0.44 ± 0.03* | 0.27 ± 0.02 |

The data represent means ± SEM (n is 6 to 7).
*Statistically significant (P < 0.05) versus control (WT/Normoxia).

7. Gene Expression Analysis in WT and HIF-2α$^{\pm}$ Lungs

Chronic hypoxia (4 weeks) decreased expression of Ang-2, eNOS and Tie-2 in lungs of both WT and HIF-2α$^{\pm}$ mice; mRNA levels of these proteins were not different between the two genotypes (Table 7). However, WT mice showed upregulation of ET-1 in the lung after exposure to hypoxia, but HIF-2α$^{\pm}$ mice did not (Table 7). Hypoxia did not increase VEGF levels in lungs of WT mice but, surprisingly, decreased VEGF mRNA levels in lungs of HIF-2α$^{\pm}$ mice (Table 7). Interestingly, expression of eNOS, the principle mediator of endothelium-dependent vasodilation in the pulmonary circulation was decreased in lungs of HIF-2α$^{\pm}$ mice under normoxic conditions, implying a possible role for HIF-2α in regulating pulmonary vascular tone. No gene inductions by hypoxia neither differences in expression between WT and HIF-2α$^{\pm}$ mice were observed for the following genes: Flk-1, Flt-1, Flt-4, NP-1, VECadherin, PlGF, VEGF-B, VEGF-C, Ang-1, PDGF-B, PDGFR-β, TGF-β, iNOS, Glut-1; LDH-A and HK-1. These data suggest that HIF-2α regulates hypoxia-induced pulmonary vascular remodeling via mediating expression of ET-1 and VEGF.

TABLE 7

Gene expression analysis in lungs of WT and HIF-2α$^{+/-}$ mice.

|  | Normoxia | | Hypoxia | |
| --- | --- | --- | --- | --- |
|  | WT | HIF-2α$^{+/-}$ | WT | HIF-2α$^{+/-}$ |
| ET-1 | 430 ± 50 | 450 ± 70 | 650 ± 50° | 460 ± 50* |
| VEGF | 430 ± 70 | 480 ± 30 | 420 ± 20 | 340 ± 20*° |
| Ang-2 | 230 ± 50 | 160 ± 20 | 90 ± 10° | 100 ± 10° |
| eNOS | 6.3 ± 1.3 | 3.2 ± 0.3* | 1.9 ± 0.3° | 1.7 ± 0.2° |
| Tie-2 | 1700 ± 100 | 1800 ± 100 | 1300 ± 100° | 1200 ± 100° |

Values are means ± SEM expressed as number of mRNA copies per 100 copies of HPRT (n is 5 to 6).
°Statistically significant (P < 0.05) versus normoxia.
*Statistically significant (P < 0.05) versus WT.

Hearts of WT mice showed increased expression of ET-1 and PDGF-B after hypoxic exposure for 4 weeks. In hearts of hypoxic HIF-2α$^{\pm}$ mice, no increase of PDGF was observed whereas ET-1 was still upregulated, however, the statistical difference was not significant and much less when compared with WT mice (Table 8). No gene inductions by hypoxia neither differences in expression between WT and HIF-2α$^{\pm}$ mice were observed for the following genes: VEGF, Flk-1, Flt-1, NP-1, Ang-1, TGF-β, eNOS, iNOS, Glut-1 and LDH-A. These data suggest a possible role for ET-1 and PDGF-B in the development of hypoxia-induced right ventricular hypertrophy.

TABLE 8

Gene expression analysis in hearts of WT and HIF-2α$^{+/-}$ mice.

|  | Normoxia | | Hypoxia | |
| --- | --- | --- | --- | --- |
|  | WT | HIF-2α$^{+/-}$ | WT | HIF-2α$^{+/-}$ |
| ET-1 | 90 ± 11 | 104 ± 12 | 242 ± 15° | 157 ± 27* |
| PDGF-B | 0.51 ± 0.08 | 0.46 ± 0.06 | 1.16 ± 0.25° | 0.54 ± 0.08* |
| PDGFR-β | 141 ± 22 | 162 ± 32 | 115 ± 24 | 72 ± 7° |

Values are means ± SEM expressed as number of mRNA copies per 100 copies of HPRT (n is 5 to 6).
°Statistically significant (P < 0.05) versus normoxia.
*Statistically significant (P < 0.05) versus WT.

8. Respiratory Distress and Lung Collapse in HIF-2α$^{-/-}$ Neonates.

Wild type new-borns adapt quickly after birth to the postnatal life. HIF-2α$^{-/-}$ new-borns in contrast develop serious respiration problems shortly after birth. Their breathing is slow and irregular accompanied with tirage caused by the diaphragm. Their chest is lift upwards reflecting the use of accessory respiratory muscles (sternocleidomastoideus and platysma). The neonates become cyanotic and eventually they die. This usually occurs within the first two hours of life. At autopsy the lungs appear collapsed in 50% of the HIF-2α$^{-/-}$ new-borns. The majority of the lungs of the other neonates appear retarded (branching structures instead of alveoli) and partially collapsed. Occasionally, in the neonates that survive a few hours, the alveoli are open but are less in number and larger then usual. Neither the lung weight nor the ratio lung/body weight is different in HIF-2α$^{-/-}$ new-borns compared with wild type littermates. The body weight at birth however is lower (Table 9). Histological examination at P0 pointed out that the lungs of HIF-2α$^{-/-}$ new-borns have a significant lower percentage of the surface filled with air (29% versus 61% in wild type) as is shown in Table 10. The airsurface at E18.5 is similar in wild types and in HIF-2α$^{-/-}$ fetus (Table 11). In 40% of the HIF-2α$^{-/-}$ new-borns the ductus Botalli is not closed.

TABLE 9

Weight of the lung and the pup at birth. Short after birth the weight of pups and of the lungs was measured. Values are expressed as the mean +/− standard error of the mean (sem).
Weight pup P0; weight lungs and ratio lung weight/weight pup

|  | Wild type (n = 7) | HIF-2α$^{-/-}$ (n = 8) | p-value |
| --- | --- | --- | --- |
| Weight pup (mg +/− SEM) | 1629 (+/−37) | 1443 (+/−40) | 0.005 |
| Weight lungs (mg +/− SEM) | 25.2 (+/−1.1) | 24 (+/−2.4) | 0.69 |
| % lung weight/weight pup (+/−SEM) | 1.55 (+/−0.049) | 1.65 (+/−0.13) | 0.48 |

Table 10: airsurface. Neonatal lungs were taken out of the thorax without perfusion to avoid distension of the tissue by perfusion. Histological sections were used to calculate the percentage of the area covered by air in alveoli related to the total area covered by air and tissue.

TABLE 11

Percentage of the total lungsurface (tissue + air) covered with air at E18.5. Histological sections were used to calculate the percentage of the area covered by fluid in alveoli related to the total area covered by air and tissue.
Ratio airsurfacel/(air + tissue)surface E18.5

| genotype | Wildtype (n = 3) | HIF-2α$^{-/-}$ (n = 3) |
|---|---|---|
| Mean | 24.9% | 23.2% |
| SEM | 2.4% | 1.5% |
| p-value | | 0.584 |

RDS was not attributable to growth retardatation, respiratory muscle dysfunction, lung hypoplasia, impaired fluid clearance, hypoxic stress or other organ defects. Only the heart rate was found to be lower in HIF-2α$^{-/-}$ fetuses, likely resulting from the reduced catecholamine production (confirming previous findings[23]). However, administration of D,L-threo-3,4-dihydrophenylserine (DOPS; a substrate that is converted to noradrenaline) to pregnant HIF-2α$^{\pm}$ females increased the heart rate and reversed the lethality of HIF-2α$^{-/-}$ embryos, but failed to reverse the fatal RDS after birth. Moreover, HIF-2α$^{\pm}$ mice, which had no signs of RDS, also had lower heart rates, making it unlikely that bradycardia or insufficient adrenergic stimulation is the primary cause of RDS.

9. Immaturity of the Alveoli and Surfactant Production in HIF-2α$^{-/-}$ Mice Immature lungs are characterised by thick alveolar septa, a less developed capillary bed and an immature alveolar epithelium. The alveolar septa are thicker in HIF-2α$^{-/-}$ neonates compared with wild types (13.6 micrometer compared with 8.1 micrometer in wild types), as shown in Table 12. The alveolar epithelium consists of more immature, glycogen rich cells. (38.64 PAS-positive cells per millimeter alveolar epithelial lining in HIF-2α$^{-/-}$ neonates versus 0.71 PAS-positive cells per millimeter alveolar epithelial lining in wild-type newborns, as shown in Table 13). Quantification shows that the number of capillaries making close contact with the alveolar lumen is decreased. In parallel the number of alveolar septa composed by a for that age appropriate dubbel capillary layer is decreased in the in HIF-2α$^{-/-}$ neonates. During normal maturation alveolar pneumocytes type 2 develop the capability to produce surfactant and surfactant associated proteins. Immunostaining for apoprotein D (one of the surfactant-associated proteins) shows a decreased number of cells positive for this protein in HIF-2α$^{-/-}$ neonates compared with wild types (3.35 versus 6.32 cells positive for apoprotein D per millimetre alveolar lining, as shown in Table 14). The lecithin/sphingomyeline ratio (3.53±0.16 in wild type lungs versus 2.84±0.23; p-value 0.0397) as well as the amount of phosphatidylcholine (184.736±21.82 nmol/10mg sample in wild type versus 111.93±14.73 nmol/10 mg sample in homozygous; p-value 0.0244) is lowered in HIF-2α$^{-/-}$ then in wild types. Semithin sections show that the number of pneumocytes type 1 is declined and the number of pneumocytes type 2 is increased in the HIF-2α–/–. The alveolar septa are to thick and have an abnormal composition. Ultrastructural analyse confirms an increased number pneumocytes type 2. Sirius red staining increased and diffuse collagen deposition in the HIF-2α–/–. MAC3 staining shows the presence of an increased number macrophages. Similar numbers of CC10-positive Clara cells were present in bronchi and bronchioli in both genotypes, and no genotypic differences were found in the presence of neuroepithelial bodies, as evidenced by PGP9.5 staining.

TABLE 12

Thickness alveolar septa. Histological sections were used to measure the thickness of the alveolar septa. Values are expressed as mean and standard error of the mean (sem).
Thickness alveolar septa (micrometer) P0

| Genotype | Wild type (n = 3) | HIfb-/- (n = 3) | PLKO-/- (n = 3) | VEGF-120 (n = 3) | VEGF-164 (n = 4) | VEGF-188 (n = 4) |
|---|---|---|---|---|---|---|
| Mean | 8.1 | 13.6 | 7.8 | 12.7 | 8.2 | 7.7 |
| SEM | 0.159 | 0.276 | 0.804 | 0.742 | 0.491 | 0.31 |
| p-value in comparence with wild type | | 6.86E−05 | 0.74 | 0.0037 | | |

TABLE 13

Pas. The length of alveoli was measured. Subsequently the number of PAS (Periodic Acid Schiff reagens) positive cells along these alveoli was counted. Values are expressed as the mean and standard error of the mean (sem) of the number of PAS positive cells per millimetre alveolar lining. Number of PAS positive cells/millimetre alveolar lining (P0)

| Genotype | Wild type (n = 3) | HIF-2α$^{-/-}$ (n = 3) | VEGF 120 (n = 3) |
|---|---|---|---|
| Mean | 0.70615 | 38.64 | 50.8 |
| SEM | 0.3616 | 7.9339 | 20.23 |
| p-value compared with wild type | | 0.0088 | 0.068 |

TABLE 14

Number of positive cells for apoprotein D at P0. The length of alveoli was measured. Subsequently the number of positive cells for apoprotein D along these alveoli was counted. Values are expressed as the mean and standard error of the mean (sem) of the number of positive cells for apoprotein D per millimetre alveolar lining. Number of cells positive for apoprotein D staining/millimetre alveolar lining (P0)

| Genotype | Wild type (n = 3) | HIF-2α$^{-/-}$ (n = 4) |
|---|---|---|
| Mean | 6.32 | 3.35 |
| SEM | 0.52 | 0.85 |
| p-value | | 0.043 |

10. Bronchogenesis and Large Vessels

At E10.5 and E13.5 the branching of bronchi appear normal. At E18.5 large bronchial structures are found in the periphery of the lung in HIF-2α-/- lungs but not in wild type lungs. The bronchi are accompanied by large vessels surrounded with smooth muscle cells at E13.5 and E18.5 (smooth muscle cell actin staining)

in wild types versus 181.6±5.7 in HIF-2α$^{-/-}$ foetus). This indicates that VEGF is regulated by HIF-2α in the alveolar epithelium. The VEGF-protein level further rises until P14. In situ hybridisation shows that VEGF-mRNA is present in the alveolar epithelium of wild type as well as HIF-2α-/- lungs. The alveolar epithelium expresses the VEGF receptor flk but not flt.

TABLE 15

Expression of VEGF-protein in the lung. Elisa-kits (R&D systems) were used to determine quantitative the mouse vascular endothelial growth factor concentrations in lungs of E16.5 and E18.5 HIF-2α$^{-/-}$ and wild types and in P0, P3, P8, P14 and adult wild type lungs (week 6). The results are expressed as mean ± standard error of the mean.

VEGF ELISA different ages (pg/mg protein)

| age | E16.5 | E18.5 | P0 | P3 | P8 | P14 | 6 weeks |
|---|---|---|---|---|---|---|---|
| WT | 119 ± 1.3 | 276 ± 7.3 | 523 ± 44.2 | 629 ± 87.2 | 935 ± 170.2 | 1102 ± 66.5 | 614 ± 64.1 |
| HIF2$^{-/-}$ | 119 ± 15.5 | 181.6 ± 5.7 | | | | | |
| p-value | 0.98 | 0.000003 | | | | | |

11. Pulmonary Angiogenesis in HIF-2α$^{-/-}$ Mice

Pulmonary development involves extensive vascular growth and remodeling, beginning during the pseudoglandular stage of development and continuing throughout all subsequent stages. Counting of vascular densities after thrombomoduline staining revealed that vascular development was comparable in both genotypes during the pseudoglandular and canalicular stages (11.5±0.7 blood vessels per alveolus in WT versus 12.4±1.3 vessels per alveolus in HIF-2α$^{-/-}$ at E17.5). There were also no genotypic differences in the formation of the proximal vessels, which follow bronchiolar branching, and distal pulmonary vessels at E18.5 (peripheral vessels covered with SMC: 2.9±0.18 vessels/100 alveoli in WT lungs versus 3.2±0.14 vessels/100 alveoli in HIF-2α$^{-/-}$ lungs, N=3, P=NS). Beyond E17.5, i.e. coincident with increased pulmonary expression of HIF-2α and VEGF (see below), vascularization of alveolar septae was impaired in HIF-2α$^{-/-}$ mice. In WT mice, capillaries lied closely juxtaposed to alveolar epithelial cells in 95% of terminal sacs (N=5), while they were distantly separated from the alveolar lumen in 30% of terminal sacs in HIF-2α$^{-/-}$ neonates (N=5; P<0.05 by Chi-Square). Microvascular basement membranes occurred in mutant mice. Transcript and/or protein levels of the VEGF receptors Flk1, Flt-1, Nrp-1, of endoglin (is increased), and of the junctional VE-cadherin were similar in mutant lungs. By pulmonary angiography, no genotypic differences could be detected in the branching, extension, patterning and architecture of the pulmonary vascular tree. Vascular densities in the heart and kidneys were comparable in newborn mice of both genotypes. Thus, HIF-2α is involved in the remodeling and expansion of the distal capillaries in the lung, while it has a more neglectible role for vascular development in other organs.

12. VEGF and VEGF-Receptor Expression

VEGF mRNA is expressed in the alveolar epithelium in the perinatal period. This expression occurs at the same time as HIF-2α expression in the alveolar epithelium. Also the protein level of VEGF gradually increases during the perinatal period (Table 15). At E16.5 there is no difference in the VEGF-protein level in wt and HIF-2α-/-. At E18.5, the HIF-2α$^{-/-}$ fetus show a significantly decrease mRNA level (Table 16; Table 17). At protein level a 40 percent reduction of VEGF is observed in HIF-2α$^{-/-}$ mice at 18.5 (276 (±7.3

13. Role of VEGF in Alveolar Epithelial Maturation

Since VEGF is a downsteam target of HIF-2α we analyzed a number of previously generated VEGF mutant mouse strains. Unfortunately, the early embryonic lethality of VEGF deficient mice (reviewed in[9]) precluded analysis of their lung development. However, ~50% of mice, selectively expressing the VEGF$_{120}$ isoform (VEGF$^{120/120}$)[28], died of RDS within a few hours after birth; their lungs were atelectatic and poorly aerated, and contained thick alveolar septa with abundant PAS-positive pneumocytes (cells per mm alveolar lining: 2±1 in WT neonates versus 51±20 in VEGF$^{120/120}$ littermates; N=3-5; P<0.05). In contrast, pulmonary development and respiration were normal in mice expressing exclusively the VEGF$_{164}$ (VEGF$^{164/164}$) or VEGF$_{188}$ (VEGF$^{188/188}$) isoform[29], or in mice lacking the VEGF homologue PlGF (PlGF$^{-/-}$)[30]. We also analyzed mice lacking the hypoxia-responsive HIF-binding site in their VEGF promotor (VEGF$^{δ/δ}$), of which a small fraction (5%) succumb within a few hours after birth, and the remaining surviving mice develop motor neuron degeneration[31]. Interestingly, the few VEGF$^{δ/δ}$ neonates that died at birth also exhibited signs of lung prematurity, although not as severe as HIF-2α$^{-/-}$ mice—likely because VEGF is regulated by other mechanisms and HIF-2α regulates the expression of other genes. Thus, absence of critical VEGF isoforms, or impaired HIF-2α-dependent VEGF regulation caused RDS. Analysis of VEGF expression revealed that pulmonary VEGF protein levels were comparable in both genotypes at E16.5. During the final stage of fetal development, VEGF levels increased ~4-fold in WT mice, but only minimally in HIF-2α$^{-/-}$ mice. By in situ hybridization, VEGF was produced by alveolar type 2 pneumocytes, while immunostaining revealed that VEGF was primarily present on the alveolar side of these cells. By ELISA, significant VEGF levels were detected in the bronchiolar alveolar lavage fluid of WT neonates (120±49 pg/mg protein). No genotypic differences were detected in pulmonary expression of PlGF (a VEGF homologue that only binds to the VEGF receptor Flt-1 but not Flk-1 [30]) or angiopoietin-1 (another vascular-specific growth factor). Double labeling revealed that Flk-1 was present in septal microvessels, but also on alkaline phosphatase-positive type 2 pneumocytes. By triple labeling, type 2 pneumocytes expressed both Flk-1 and HIF-2α. Flt-1 was detectable on capillaries and colocalized with the endothelial marker CD31 on adjacent sections, while the VEGF$_{165}$-isoform selective receptor neuropilin-1 was undetectable. Notably, freshly isolated type 2 pneumocytes also expressed Flk-1 transcripts and responded to VEGF by increasing their expression of SP-B and SP-C (copies/100 copies β-actin for SP-B and SP-C: 15±1 and 12±1 after saline versus 27±4 and 21±4 after VEGF; N=4-6; P<0.05). Thus, surfactant-producing alveolar type 2 cells produce VEGF in a HIF-2α-dependent manner and are responsive to VEGF.

TABLE 16

Lungs are taken from fetus at E18.5. Real Time PCR was used to quantify the amount of mRNA for several genes. The results are expressed as mean ± standard error of the mean. mRNA expression in E18.5 lungs

| | Wild type (mean +/− SEM) | HIF-2α$^{-/-}$ (mean +/− SEM) | p-value |
|---|---|---|---|
| Angiopoietin-1 | 52.8 (+/−2.8) | 65.1 (+/−11.2) | 0.320 |
| Endothelin-1 | 74.8 (+/−8.0) | 55.6 (+/−6.0) | 0.092 |
| Flt-1 | 32.3 (+/−5.1) | 27.1 (+/−3.2) | 0.412 |
| Flt-4 | 12.7 (+/−0.8) | 17.2 (+/−2.4) | 0.088 |
| Glut-1 | 188 (+/−22) | 156 (+/−11) | 0.230 |
| HIF-1 | 104.0 (+/−16.2) | 92.9 (+/−16.2) | 0.586 |
| LDH-A | 29.7 (+/−4.3) | 22.5 (+/−1.6) | 0.157 |
| NP-1 | 34.46 (+/−5.83) | 35.62 (+/−4.42) | 0.878 |
| TEK | 109.2 (+/−11.4) | 133.0 (+/−14.7) | 0.236 |
| VEGF | 33.2 (+/−2.3) | 20.3 (+/−1.7) | 0.018 |
| ENOS | 11.9 (+/−0.3) | 23.0 (+/−3.2) | 0.008 |
| INOS | 27.3 (+/−3.0) | 15.1 (+/−0.8) | 0.004 |
| PDGF | 7.83 (+/−0.69) | 7.70 (+/−0.97) | 0.916 |
| PDGFbetaR | 131 (+/−8) | 215 (+/−36) | 0.052 |
| PLGF | 8.32 (+/−0.78) | 9.99 (+/−0.92) | 0.202 |
| TGFbeta | 28.6 (+/−1.1) | 40.7 (+/−3.7) | 0.015 |

TABLE 17

Gene expression in the lung at E18.5. Lungs are taken from fetus at E18.5. Real Time PCR was used to quantify the amount of mRNA for several genes. The results are expressed as mean ± standard error of the mean. Wild type lungs (n = 6) and HIF-2α$^{-/-}$ lungs (n = 6). mRNA expression VEGF isoforms in E18.5 lungs

| | Wild type (mean ± SEM) | HIF-2α$^{-/-}$ (mean ± SEM) | p-value |
|---|---|---|---|
| VEGF 120 | 64 ± 4 | 54 ± 7 | 0.104 |
| VEGF 165 | 52 ± 2 | 29 ± 8 | 0.0001 |
| VEGF 189 | 136 ± 15 | 79 ± 14 | 0.0156 |

14. mRNA Expression of Other Hypoxia Regulated Genes iNOS, a gene suggest to be regulated by hypoxia inducible factor 1 in the heart is decreased at the mRNA level in HIF-2α$^{-/-}$ lungs at 18.5 (15.1 in HIF-2α$^{-/-}$ versus 27.3 in wildtype). The eNOS-mRNA level in contrast is higher in the HIF-2α$^{-/-}$ lungs (23.0 versus 11.9). The mRNA levels of endothelin-1, glut-1, tek, LDH-A, neuropilin-1, fit-1, all genes known to be regulated by hypoxia inducible factors are not different in lungs of E18.5 HIF-2α$^{-/-}$ foetus (as shown in Table 16). The mRNA level of hypoxia inducible factor 1 α is not different in HIF-2α$^{-/-}$ versus wild types. HIF-2α transcript levels were comparable in the lung, heart and kidneys in E16.5 WT fetuses. Thereafter, expression of HIF-2α increased more than 5-fold in the lungs but less than 2-fold in the heart and kidneys. Double-immunostaining for alkaline phosphatase (a marker of type 2 pneumocytes) and HIF-2α revealed that alveolar type 2 pneumocytes abundantly expressed HIF-2α, although other cells in alveolar septa, presumably endothelial and mesenchymal cells, also expressed HIF-2α.

15. mRNA Expression of Genes Known to be Involved in Lung Development

Several clinical studies showed that TGFbeta is increased in respiratory distress syndrome especially in the group predisposed for chronic lung disease. It is presumed that this higher TGFbeta levels are correlated with lung fibrosis. In HIF-2α $^{-/-}$ lungs (at E18.5) the TGFbeta mRNA is increased (40.7 versus 28.6 in wild type). Platelet derived growth factor (PDGF) and its receptor (PDGFbetaR) are involved in the development of emphysematous lesion (as well in null mutations as in overexpression studies). PDGFis not different expressed in HIF-2α$^{-/-}$ lungs. The PDGFbetaR-mRNA level is increased in the HIF-2α$^{-/-}$ lungs (Table 16).

16. Intra-Amniotic VEGF Administration Prevents RDS in Preterm WT Fetuses

Twenty hours after intraamniotic injection of Evans blue at E 16.5, the lungs of 53% of the injected fetus turned blue (n=19). In contrast all the lungs of fetus injected at E17.5 turned blue after 5 hours (n=11). Therefore we concluded that only injection at E17.5 is reliable for the administration of proteins by intra-amniotic injection. Within 5 hours after intra-amniotic injection at E17.5 of 500 ng human VEGF$_{165}$ (hVEGF) per E17.5 fetus, 8±1 ng hVEGF/mg protein or 14±1 ng hVEGF was recovered in the fetal lungs (background of murine VEGF was <0.1%). The amount of hVEGF used for intra-amniotic injection was calculated as follows: the volume of the amniotic fluid and fetal lungs/guts was estimated to be ~500 μl. Taking into account that VEGF might be rapidly degraded or cleared, a dose of 500 ng was used to achieve an initial maximal dose of ~1 μg/ml, which is at least 10-fold higher than an effective concentration in vitro (when delivered by intra-amniotic route, a 10- to 100-fold excess of surfactant is administered). The effect of VEGF administration on lung maturation of WT fetuses in vivo was then tested by injection of VEGF in the amniotic cavity at E17.5 and subsequent delivery of preterm pups by Caesarean section at E18.5. VEGF delivery resulted in an APGAR score of 7.5±0.7 and 8±0.4 after 5 and 10 minutes, respectively (N=8), which is better than the score after saline (5±0.3 after 5 and 10 minutes in saline-treated pups; N=10, P<0.005). In contrast to the 24 saline-treated pups, of which 75% remained completely immobile after 20 minutes, 60% of 24 VEGF-treated pups breathed spontaneously and regularly, had a pink skin color after 10 minutes, and actively moved their limbs after 20 minutes (N=24; P<0.02). As a result of the improved aeration after VEGF (Table 18), inflated VEGF-treated lungs floated, while atelectatic control lungs sank to the bottom, when transferred to a water-filled recipient. After VEGF treatment, alveolar septa were thinner, PAS-positive glycogen stores were mobilized (Table 18) and surfactant production was increased (phosphatidylcholine per lung: 180±14 nmol in control versus 220±10 nmol after VEGF; N=5, P<0.05). In addition, the number of septa with a single layer of vessels, lying closely apposed to the alveolar lumen was increased (<0.2% in control versus 8±2% after VEGF; N=10; P<0.002). The therapeutic effect of VEGF was specific, since intra-amniotic injection of PIGF, a specific ligand of Flt-1 but not Flk-1, was ineffective (Table 18). Notably, VEGF was comparably effective to the glucocorticoid dexamethasone (0.8 mg/kg), administered to pregnant mice at gestational day 15.5 and 16.5. Dexamethasone improved the APGAR score to 6.7±0.7 and 8.4±0.4 after 5 and 10 minutes, respectively (N=71; P=NS versus VEGF; P<0.005 versus saline for 5 and 10 minutes, respectively) and stimulated lung aeration (57±3% after dexamethasone versus 58±1% after VEGF; N=3-9; P=NS; as compared to 39±2% after saline; Table 18). VEGF was slightly more efficient in thinning of the septa than dexamethasone (10±0.1 μm after dexamethasone versus 8±0.1 μm after VEGF, N=3-9; P<0.05). Notably, pulmonary VEGF levels were increased by a low dose, but suppressed by a high dose of dexamethasone (pg/mg protein at E18.5: 270±12 after saline versus 330±9 and 210±18 after 0.8 or 2.4 mg/kg dexamethasone, respectively; N=5-11; P<0.05 versus saline). Thus, intra-uterine VEGF improved fetal lung maturation and prevented RDS.

17. Intra-Tracheal VEGF Treatment Improves Pulmonary Maturation in Premature WT Newborns To examine whether hVEGF could also prevent respiratory distress preterm newborns, E17.5 WT pups were delivered by caesarean section and treated intra-tracheally with saline or 500 ng hVEGF. Since injected pups were often cannibalized by their foster mothers, pups were monitored in isolation from a foster mother, which limited the clinical to maximum period of 10 hours (thereafter, pups started to become dehydrated and deprived of nutrients). After Caesarian delivery at E17.5, ~60% of preterm pups had an aerated lung area of less than 25% and died immediately after birth (category A), while another ~10% of preterm pups ventilated well and were normally oxygenated (category B). The remaining ~30% of preterm pups had an aerated lung area of 39±2% and suffered severe RDS. These pups were able to live for at least 6 hours although, ultimately, they succumbed to fatal exhaustion (category C). Only mice of class C were intratracheally injected with VEGF (500 ng/pup). To allocate pups to categories A, B and C, newborns were monitored for 30 minutes after Caesarean section, when their lung function and clinical condition was easily scored. Intra-tracheal VEGF administration prevented RDS in preterm pups of category C. Within 4-6 hours after VEGF administration, breathing became easier and more regular, skin color turned pink and pups moved more actively. As a result, a third of the VEGF-treated pups (N=22), but none of the controls (N=14), survived for up to 20 hours when they were sacrificed (P<0.03). Histological analysis after 6 hours revealed that VEGF-treatment improved lung aeration, accelerated alveolar septal thinning, and stimulated conversion of glycogen stores, as evidenced by the disappearance of PAS-positive cells (Table 18). No differences were found in the number of cells expressing SP-B (positive cells/mm alveolus: 2.6±0.8 after saline versus 3.5±0.9 after VEGF; N=4; P=NS). Considering that intra-tracheally delivered VEGF could only reach ventilated lung areas (~50% of the lung), and taking the short duration of VEGF exposure (6 hours) and the young fetal age (E17.5) into consideration, the observed improvement of the clinical condition and lung maturation is remarkable.

18. Effect of VEGF Treatment on the Maturation of the Lung

Survival after premature birth was not significantly different in mice treated with hVEGF165 (100%, n=22) then in mice treated with saline (92%, n=24). However significantly more treated premature pups (63%, n=22) then control premature pups (25% n=24) moved spontaneously (p<0.02). Macroscopically threaten lungs were more expanded then placebo-treated lung (78%±5 in treated (n=9) versus 43%±10 in untreated lungs (n=10); p<0.01). Histological analysis confirmed the improved expansion of the hVEGF 165 treated lungs. The percentage of the total lungsurface covered with air was 58%±1 in treated lungs versus 39%±2 in placebo treated lungs (p<0.001). In addition the alveolar septa of the treated lungs were thin (8.4±0.1 micrometer, n=9) compared to placebo treated lungs (12.4±0.4 micrometer, n=10) (p<0.001). In addition the number of PAS positive cells was lower in hVEGF165 treated (23±4)(n=5) then in control treated lungs (72±11)(n=5)(p<0.005). Treatment with hVEGF did not increase the number of blood vessel (16.9±0.6 blood vessels/alveolus in hVEGF versus 17.2±0.5 in saline treated lungs). The percentage of alveoli with a double layer of blood vessels was similar in both groups (97%±2 in saline treated versus 92%±2 in VEGF treated lungs). During expansion of the lung the septa with a double layer of capillaries change into more thin septa with a single layer of blood vessels in close contact with the alveolar epithelium. Due to the increased expansion of the lungs in the hVEGF treated lungs, 8±2% of the alveoli in the hVEGF treated versus 0.2±0.2% of the alveoli in the saline treated group had a single layer of blood vessels. (p<0.002)

19. Inhibition of Flk-1 Impairs Fetal Lung Maturation

To analyze which VEGF receptor mediated lung maturation, neutralizing anti-Flk1 antibodies (preventing binding of VEGF to Flk-1 [30,31]) or anti-Flt-1 antibodies (blocking binding of VEGF and PlGF to Flt1 [30,31]) were intra-amniotically injected in WT fetuses at E17.5, and pups were delivered by Caesarean section at E18.5. Anti-Flt-1 antibodies were ineffective, but anti-Flk-1 antibodies prevented the thinning of the alveolar septa and the disappearance of PAS-positive cells (Table 3). Even though anti-Flk-1 treated pups were able to aerate their lungs (Table 18) and had a normal APGAR score after 5 minutes (4.4±0.9; N=9; P=NS), two pups subsequently succumbed to RDS. By immunostaining, intra-amniotically injected antibodies remained restricted to the alveolar compartment, suggesting that the observed effects on lung maturation were due to inhibition of alveolar VEGF. Taken together, Flk-1, not Flt-1, mediates the effect of endogenous VEGF on lung maturation in vivo.

TABLE 18

Treatment with VEGF improves lung maturation in preterm WT mice.

|  | Intra-amniotic injection at E17.5 → preterm delivery at E18.5 | | | | | | Intra-tracheal injection after delivery at E17.5 | |
| --- | --- | --- | --- | --- | --- | --- | --- | --- |
|  | Saline | VEGF | PlGF | IgG | Anti-Flt1 | Anti-Flk1 | Saline | VEGF |
| Aerated lung area (% of total) | 39 ± 2 | 58 ± 1* | 41 ± 1 | 42 ± 2 | 41 ± 1 | 37 ± 4 | 44 ± 2 | 52 ± 3* |

TABLE 18-continued

Treatment with VEGF improves lung maturation in preterm WT mice.

| | Intra-amniotic injection at E17.5 → preterm delivery at E18.5 | | | | | | Intra-tracheal injection after delivery at E17.5 | |
|---|---|---|---|---|---|---|---|---|
| | Saline | VEGF | PlGF | IgG | Anti-Flt1 | Anti-Flk1 | Saline | VEGF |
| Alveolar septal thickness (μm) | 12 ± 0.4 | 8 ± 0.1* | 13 ± 0.1 | 13 ± 0.2 | 13 ± 0.1 | 15 ± 0.5* | 18 ± 1 | 15 ± 1* |
| PAS-positive cells/mm alveolus (% of control) | 100 | 38 ± 6* | 78 ± 6 | 100 | 118 ± 13 | 208 ± 18* | 100 | 55 ± 7* |
| Number of blood vessel/alveolus | 17 ± 0.7 | 17 ± 0.2 | 17 ± 0.9 | 16 ± 0.5 | 16 ± 1.0 | 16 ± 0.5 | 13 ± 0.4 | 14 ± 0.3 |

Values represent the mean ± SEM of measurements in 5 to 10 mice.
*P < 0.05 versus littermates treated with saline or IgG by t-test. For intra-amniotic injection, fetuses were injected at E17.5 in utero, and premature pups were then delivered by Caesarean section at E18.5. For intra-tracheal injection, premature E17.5 fetues were delivered by Caesarean section.

20. Safety of Pulmonary VEGF Treatment

Administration of recombinant human VEGF (hVEGF) to the airways may not necessarily cause the same adverse effects on vascular leakage as systemic administration or adenoviral VEGF gene transfer to the airway cells[33], because the alveolar epithelium is less permeable than the endothelium. When 1 μg hVEGF was intra-tracheally administered, resulting in an estimated concentration of 10 μg/ml alveolar fluid, less than <0.1% of the hVEGF was recovered in the plasma after 1 hour (500±60 pg/ml hVEGF as compared to 50±4 pg/ml murine VEGF in plasma of uninjected pups). After 3 and 5 hours, hVEGF plasma levels were undetectable (<2 pg/ml), confirming previous findings that VEGF remaines restricted to the alveolar compartment with minor spill-over to the interstitium and circulation[12]. Similar findings were obtained after intra-amniotic injection of hVEGF. Neither intra-amniotic nor intratracheal VEGF stimulated angiogenesis in alveolar septa (Table 18), vascular leakage (analyzed by Western blotting the amount of extravasated IgG in perfused lungs) or bronchial edema. There were also no microscopic abnormalities, leakiness or neovascular growth in the gastro-intestinal tract, placenta or fetal membrane after intra-amniotic delivery.

Materials and Methods

1. Mapping of the HIF-2α Gene and Construction of a Targeting Vector

A genomic BAC clone containing the murine HIF-2α gene was obtained from Research Genetics, Inc. (Huntsville, Ala., USA). BAC-DNA preparations were performed using the following protocol: Bacterial pellets from overnight cultures were resuspended in 10 ml of 50 mM Tris-HCl pH 8.0 containing 10 mM EDTA (ethylene di-amino tetra-acetate) and 0.1 mg/ml RNase A. The cell suspension was lysed with 10 ml of 200 mM NaOH/1% SDS during 5 minutes and afterwards neutralized with 10 ml of 3.0 M potassium acetate (pH 5.5). After centrifugation, an equal volume of isopropanol was added to the supernatant to precipitate the DNA. DNA pellets were dissolved in 10 mM Tris-HCl pH 8.0 containing 1 mM EDTA; phenol/chloroform extractions were performed to purify the DNA solutions. BAC-DNA was digested overnight with different restriction enzymes (single and double digests) and loaded on 1% agarose gels for electrophoresis. After Southern blotting of DNA on Genescreen nylon membranes (NEN Life Science Products Inc, Boston, Mass., USA) and hybridization (using QuikHyb hybridization solution (Stratagene, La Jolla, Calif., USA)) with radioactive $^{32}$P-labeled probes, exposure of radiation-sensitive films (Kodak, Rochester, N.Y., USA) to the hybridized membranes allowed physical mapping of the HIF-2α gene. DNA fragments in the vicinity of exon 2 of the HIF-2α gene were digested with restriction enzymes, separated by gel electrophoresis, purified (Gel purification kit, Qiagen, Valencia, Calif., USA) and subcloned into pBluescript (Stratagene, La Jolla, Calif., USA) using the classical cloning techniques (ligation of DNA fragments at 14° C. using T4 DNA ligase (New England Biolabs Inc, Beverly, Mass., USA) in 50 mM Tris-Hcl pH 7.5 containing 1 mM DTT (dithiothreitol), 1 mM ATP and 10 mM $MgCl_2$; transformation of competent *E. coli* DH5α cells with ligation products). These cloned DNA fragments were used for construction of a targeting vector with 10 kb homology to inactivate the HIF-2α gene.

2. ES Cell Culture and Media

Undifferentiated embryonic stem (ES) cells were cultured in ES cell medium (Dulbecco's modified Eagle medium (DMEM) containing 100 IU/ml penicillin, 100 μg/ml streptomycin, 0.001% β-mercapto-ethanol, 2 mM glutamine, 1 mM Na-pyruvate, 1% of a 100× solution of non-essential amino acids (NEAA) and 10 ng/ml leukemia inhibitory factor (LIF)), supplemented with 15% heat-inactivated fetal calf serum (FCS), on 0.1% gelatin-coated 10-cm culture dishes, containing mitomycin C-inactivated primary embryonic fibroblasts (mitomycin C-inactivation: 10 μg/ml for 3 hours). The cells were cultured in a humidified $CO_2$ incubator at 37° C., 90% humidity, and with 95% air and 5% $CO_2$, and refed daily with fresh ES cell medium. When confluent, ES cells were washed with phosphate buffered saline (PBS), trypsinized with 0.25% trypsin and 0.02% EDTA for 5 minutes at 37° C. (5% $CO_2$) and split at a ratio 1:4 to 1:8. For storage of ES cells in liquid $N_2$, ES cells were frozen in ES cell medium containing 35% fetal calf serum and 10% dimethlyl sulfoxide (DMSO). DMEM, NEAA, penicillin/streptocmycin, Na-pyruvate, glutamin, tissue culture-grade PBS, LIF-ESGRO and trypsin/EDTA were from Life Technologies, Rockville, Md., USA; β-mercapto-ethanol and DMSO from Sigma, Bornem, Belgium; FCS from Hyclone, Logan, Utah, USA; and MitomycinC Kyowa was from NTL, Brussel, Belgium.

3. Generation of HIF-2α Deficient ES Cells and Mice

After linearization with NotI, the targeting vector was purified for electroporation in male R1 ES cells (provided by A. Nagy, Samuel Lunenfeld Institute, Toronto, Canada). Therefore, 20 µl linearized DNA (1 µg/µl) and $6.10^6$ ES cells, suspended in 0.8 ml PBS, were gently mixed in a 0.4-cm cuvette and immediately zapped at 250 V and 500 µF. The electroporated ES cells were then diluted in 10 ml ES cell culture medium and plated out on a 10-cm dish containing embryonic fibroblast feeder cells. For one electroporation, 5 cuvettes were prepared and processed in this way. After 24 h, selection with 200 µg/ml geneticin (G418, Life Technologies, Rockville, Md., USA) was started for 8 days. At day 3 of selection, negative selection with Gancyclovir (1 µM final concentration) was also started. Picking and transfer of individual G418/Gancyclovir double-resistant colonies to 96-well plates was started at day 9 and continued for 3 days. When ES clones were confluent, the cells were replica-plated in threefold; two aliquots of each clone were plated in a 96-well on separate 96-well plates for freezing, while a third aliquot was seeded into a 48-well and grown for DNA preparation used for genotyping. ES cell lysis was accomplished with Proteinase K (250 µg/ml; Boehringer Mannheim, Mannheim, Germany) in 100 mM Tris-HCl, 5 mM EDTA, 0.2% SDS and 0.2 M NaCl (0.5 ml lysis buffer per 48-well). Genomic DNA was precipitated after addition of an equal volume isopropanol and redissolved in 100-200 µl TE buffer (10 mM Tris-HCl pH 8.0 with 1 mM EDTA). Homologous recombinants were identified by diagnostic restriction digests/Southern blot analysis. Homozygous HIF-2α$^{-/-}$ ES cells were obtained after selection of HIF-2α$^±$ ES cells at high G418 concentration (1.8 mg/ml) during 8 days and identified by Southern blot analysis. HIF-2α$^±$ ES clones were used for generation of transgenic mice via aggregation with diploid embryos. Therefore, 2.5 days old 8-cell stage embryos (morula stage) were collected from the oviduct of pregnant Swiss females and aggregated with HIF-2α$^±$ ES cell clumps containing 8-15 cells after removal of the zona pellucida with an acidic buffer (pH 2.5). Aggregated embryos were cultured during 2 days at 37° C. (5% $CO_2$) and subsequently, after having reached the blastocyst stage, reimplanted in the uterus of pseudo-pregnant (2.5 days post-coitus) foster mothers (20 embryos per female) to generate chimaeric mice. Male chimaeric mice were test bred for germline transmission with wild type Swiss females. Germline offspring was identified by their agouti coat colour. HIF-2α$^±$ animals among the germline offspring were identified by Southern blot analysis of genomic DNA isolated from tails, and were intercrossed to obtain homozygous HIF-2α$^{-/-}$ progeny.

4. RT-PCR and Immunoblot Analysis

Inactivation of the HIF-2α gene was confirmed at the RNA and antigen level respectively by reverse transcriptase PCR (RT-PCR) and immunoblot analysis. Total RNA was extracted from wild type and HIF-2α–/– ES cells using TRIZOL reagent (Life Technologies, Rockville, Md., USA), purified by phenol/chloroform extraction and precipitated with isopropanol. DNase treatment of purified RNA was performed at 37° C. for 15 minutes with DNaseI (Amersham Pharmacia Biotech, Uppsala, Sweden) in 40 mM Tris-HCl pH 7.5 and 6 mM MgCl2. RNA was dissolved in RNase-free H2O and transcribed in cDNA with reverse transcriptase Superscript II (Life Technologies, Rockville, Md., USA). Primer A (5'-ACGGAACTCCAGGTCCCTTGTCGCTGC-3' (SEQ ID NO: 1)) (exon 1) and primer B (5'-ACAG-GAGCTTATGTGTCCGAAGGAAGC-3' (SEQ ID NO: 2)) (exon 2) were used for PCR on cDNA to amplify a HIF-2α specific 531-bp fragment. Expression of the HPRT gene was used for normalization; therefore, a HPRT specific 374-bp fragment was amplified using primer hprt190 (5'-GTCGC-CCTCTGTGTGCTCAAGGGGG-GC-3' (SEQ ID NO: 3)) and primer hprt563 (5'-AAACTTGTCTG-GAATTTCAAATCCAAC-3' (SEQ ID NO: 4)). Protein extraction and immunoblot analysis were performed as previously described. Briefly, ES cells were washed with ice-cold PBS, scraped from the dishes and homogenized with an IKA Ultra-turrax T8 homogenizer (Janke & Kunkel, Stauffen, Germany) in an 8 M urea buffer, containing 10% glycerol, 1% SDS (sodium dodecyl sulphate), 5 mM DTT and 10 mM Tris-HCl (pH 6.8). Per 50 ml of lysis buffer, 1 tablet of the protease inhibitor cocktail CompleteTM was added (Boehringer Mannheim, Mannheim, Germany). Protein concentrations of the extracts were quantified with the BCA protein assay (Pierce, Rockford, Ill., USA), which is based on the protein-mediated reduction of $Cu^{2+}$ to $Cu^{1+}$ in basic medium and the subsequent formation of a purple complex between $Cu^{1+}$ and bicinchoninic acid (BCA). This complex can be quantified by spectrophotometric analysis at 560 nm. Proteins were loaded on SDS/6% polyacrylamide gels for electrophoresis and afterwards transferred to Immobilon P membranes (Millipore, Bedford, Mass., USA) in 10 mM Tris, 100 mM glycine, 10% methanol and 0.05% SDS. Membranes were blocked with PBS containing 5% fat-free milk and 0.1% Tween 20. MoAb28b and 190b monoclonal antibodies (provided by Dr. P. Maxwell and Dr. P. Ratcliffe, Institute of Molecular Medicine, John Radcliffe Hospital, Oxford, UK) were used for binding with HIF-1α and HIF-2α respectively. Secondary goat anti-mouse antibodies (DAKO, Carpinteria, Calif., USA) conjugated with HRP (horseradish peroxidase) were used for detection by chemoluminescence. Immunoblot analysis was done in collaboration with Dr. P. H. Maxwell and Dr. P. J. Ratcliffe (Institute of Molecular Medicine, John Radcliffe Hospital, Oxford, UK).

5. Mouse Model for Pulmonary Hypertension

Female mice of 8 weeks old were weighed and placed in a tightly sealed chamber under normobaric hypoxia (10% $O_2$), which was maintained by a continuous inflow of 2 l/min $N_2$ and 2 l/min normal air (20% $O_2$). The chamber was opened every 7 days for 10 minutes to clean the cages and to add food and water; mice were kept at these conditions for 4 weeks. Control mice were kept for 4 weeks in normal air (20% $O_2$). After 28 days, mice were weighed, anaesthetized and used for right ventricular pressure measurements. After collection of blood for hematocrit determination, hearts and lungs were dissected and used for gene expression analysis (real time PCR), histological analysis and determination of right ventricular hypertrophy.

6. Blood Pressure Measurements

Before performing measurements, mice were reoxygenated by returning them to room air for 1 hour and subsequently anaesthetized with 1.4 mg/kg urethane. The right ventricular pressures were measured in anaesthetized ventilated mice by transthoracic puncture using high-fidelity pressure micromanometers (SPR-671; Millar Instruments, Houston, Texas) at controlled normal body temperatures. Correct position of the pressure manometers in the right ventricle was verified by pressure readings and confirmed by postmortem examination. Hemodynamic measurements were amplified (Siemens Pressure Amplifier 863, Elema, Solna, Sweden) and analyzed on a PC-based computer program (Windaq Software vs 1.37, Dataq Instruments Inc, Akron, Ohio, USA).

7. Hematocrit and Right Ventricular Hypertrophy Measurement

Blood samples were collected from the vena cava and anticoagulated with sodium citrate (4.14% solution in 0.1 M PBS (pH 7)) and analyzed for hematocrit level and hemoglobin content using an automated cell counter (Abbott Cell-Dyn 1330 system, Abbott Park, Ill., USA). Hearts were dissected and right ventricular wall was removed from the left ventricle and septum after removal of the atria. Both ventricles were dried at 55° C. for 3 to 6 days (until weight difference between 2 consecutive days was less than 0.2 mg) and subsequently weighed. Results were expressed as the ratio of right ventricle weight over left ventricle plus septum weight or as the ratio of right ventricle weight over total body weight.

8. Histological Analysis of the Lungs

Mice were anaesthetized with pentobarbital (60 mg/kg) and perfused via cardiac puncture with saline to remove the blood followed by 1% paraformaldehyde in 0.1 M PBS (pH 7) at 100 cm $H_2O$ pressure. Subsequently, the trachea was cannulated and the airways were perfused with 1% paraformaldehyde in 0.1 M PBS (pH 7) at 25 cm $H_2O$ pressure. Lungs and heart were removed "en bloc" and post-fixed in 1% paraformaldehyde in 0.1 M PBS (pH 7) for 12 hours. After dehydratation, lungs and hearts were embedded in paraffin; 7 μm sections were used for histological stainings (haematoxylin and eosin). Hart's elastin staining was performed for visualization of internal elastic lamina (IEL) and external elastic lamina (EEL). Rabbit antibodies against murine thrombomodulin (a gift from Dr. R. Jackman, Harvard University, Boston, Mass., USA) and mouse antibodies against murine smooth muscle cell α-actin (DAKO, Carpinteria, Calif., USA) were used for stainings of endothelial and smooth muscle cells respectively (see section 10). Hypoxia-induced pulmonary vascular remodeling was assessed by counting the number of non-muscularized (only IEL), partially muscularized (IEL plus incomplete EEL) and fully muscularized (IEL and complete EEL) peripheral vessels (located distal to the bronchi) per 100 alveoli using the Quantimet Q600 imaging system (Leica imaging systems Ltd, Cambridge, UK) (30).

9. Murine and Human VEGF Immunoassay

Elisa-kits (R&D systems) were used to determine quantitative the mouse vascular endothelial growth factor concentrations in lungs of E16.5 and E18.5 HIF-2α$^{-/-}$ and wild types and in P0, P3, P8, P14 and adult wild type lungs (week 6). Human VEGF immunoassay was use to determine the quantity of injected hVEGF that reached the lungs.

10. Histology and Immunostaining

Lungs of E18.5 and P0 or total foetus (E10.5, E13.5 and E18.5) were fixed in 1% paraformaldehyde O.N. and paraffin embedded. Immunostaining for thrombomodulin, smooth muscle cell actin and apoprotein D, H&E and PAS-staining were performed on paraffin sections. Immunostaining for flk and flt were done on sections of unfixed in OCT frozen E18.5 lungs. Quantification of the number positive PAS cells and positive cells for apoprotein was calculated per millimetre of alveolar epithelial lining to correct for the collapse that occurred in the HIF-2α$^{-/-}$ and VEGF$^{120/120}$ lungs. The septal thickness and the percentage of the total lungsurface (tissue+air) covered with air where determined using the Quantimet Q600 imaging system (Leica imaging systems Ltd, Cambridge, UK) on at least 5 optical fields.

11. Measurement of Surfactant Phospholipids

Lung tissue was homogenized (Polytron PTA7 aggregate; Kinetica Benelux, Best, The Netherlands) in 1.9 ml of chloroform/methanol/water (5/10/4; v/v). The device was rinsed with 1.9 ml of the mixture and the rinse was added to the homogenate. Aliquots of the lipid extracts[52] were analyzed for total phosphate[53] and with or without solid phase extraction of the neutral phospholipids on an amino-propyl matrix[54] (NH-BondElut, 500 mg; Varian Benelux, Leersum, The Netherlands), subjected to thin layer chromatography (0.25 mm silica 60G plates; solvent chloroform/methanol/ acetic acid/0.9% (w/v) NaCl (50/25/8/2.5; v/v). Spots corresponding to sphingomyelin and phosphatidylcholine were scraped in Pyrex tubes, followed by wet ashing and phosphate analysis[53].

12. Intra-Amniotic and Intratracheal Injections

For intra-amniotic injections, pregnant WT Swiss mice were anesthesized using isofluran and, after laparatomy, 10 μl of Evans blue (final concentration 0.5%), saline, hVEGF$_{165}$ (R&D Systems; 0.5 μg/10 μl saline) or hPlGF-2 (Reliatech, Braunschweig, Germany; 0.5 μg/10 μl saline) were injected in the amniotic cavity of E17.5 fetuses through the uterine wall, taking great care not to injure the fetuses, placenta or fetal membranes. Pups were prematurely delivered by Caesarean section at E18.5 (one day before the end of gestation), and scored for respiration and skin oxygenation (APGAR-like score), spontaneous movements and survival during the first 20 minutes, before lungs were dissected and processed for morphological analysis. For intra-tracheal injections, WT E17.5 fetuses were delivered by Caesarean section, surviving pups were anesthesized on ice and, through a small skin incision, intratracheally injected with hVEGF$_{165}$ (0.5 μg/5 μl) or saline (5 μl). Survival of the premature pups was followed during 20 hours, while in other pups, lungs were analyzed histologically after 6 hours of intratracheal injection.

13. In vivo Assessment of Murine Embryonic Heart Rate

Pregnant HIF-2α$^{±}$ mothers at gestation day 18.5 were used for in vivo ultrasonic determination of embryonic heart rate as described[55]. Briefly, after maternal anesthesia (urethane i.p.), a midline abdominal incision was made and the uterine horns were exposed. To maintain stable embryonic and maternal temperature, the experimental set-up consisted of a temperature-regulating water bath (37° C.), filled with oxygenated (95% $O_2$ and 5% $CO_2$) Krebs-Henseleit buffer. The female was placed in a supine position in the water bath, allowing to expose the uterine horns on a horizontal plane. Non-invasive pulsed Doppler measurements on all E18.5 embryos were perfomed in utero within 10 minutes, using the Hewlett Packard Sonos 5500 echocardiographic device (Brussels, Belgium), equipped with a linear 15 MHz transducer. Three sequential beats were averaged for determination of embryonic heart rates.

14. Determination of Catecholamine Levels

Adrenal glands and organs of Zuckerkandl from neonates were snap frozen, stored at −80° C., homogenized on ice in 1 ml of 0.1M perchloric acid containing 0.3% glutathione and 5 μg/l 3,4-dihydroxybenzylamine (as internal standard) and centrifuged at 4° C. for 10 minutes (19,000 g). Catecholamines were eluted from alumina with 0.1 M perchloric acid, 0.3% glutathione, and quantitated by high pressure liquid chromatography[23]. For catecholamine rescue experiments, D,L-threo-3,4-dihydrophenylserine (DOPS, 1 mg/ml) was supplemented to the drinking water (containing 2 mg/ml ascorbic acid in bottles shielded from light and changed daily) of pregnant females from gestation day 8.5 until birth of the pups[23].

15. Isolation and Culture of Type 2 Pneumocytes

Type 2 pneumocytes were isolated from Wistar rat lungs according to the previously described methods[56]. Human VEGF (200 ng/ml, R&D Systems) was added to the culture medium. SP-B and SP-C levels were measured after 30 hours.

REFERENCES

1. Goldenberg, R. L., Hauth, J. C. & Andrews, W. W. Intrauterine infection and preterm delivery. *N Engl J Med* 342, 1500-7. (2000).
2. Bhakoo, O. N., Narang, A., Karthikeyan, G. & Kumar, P. Spectrum of respiratory distress in very low birthweight neonates. *Indian J Pediatr* 67, 803-4. (2000).
3. Greenough, A. Expanded use of surfactant replacement therapy. *Eur J Pediatr* 159, 635-40. (2000).
4. Bourbon, J. R., Rieutort, M., Engle, M. J. & Farrell, P. M. Utilization of glycogen for phospholipid synthesis in fetal rat lung. *Biochim Biophys Acta* 712, 382-9. (1982).
5. Kennedy, J. D. Lung function outcome in children of premature birth. *J Paediatr Child Health* 35, 516-21. (1999).
6. Walfisch, A., Hallak, M. & Mazor, M. Multiple courses of antenatal steroids: risks and benefits. *Obstet Gynecol* 98, 491-7. (2001).
7. Robertson, B. & Halliday, H. L. Principles of surfactant replacement. *Biochim Biophys Acta* 1408, 346-61. (1998).
8. Jakkula, M. et al. Inhibition of angiogenesis decreases alveolarization in the developing rat lung. *Am J Physiol Lung Cell Mol Physiol* 279, L600-7. (2000).
9. Ferrara, N. Role of vascular endothelial growth factor in regulation of physiological angiogenesis. *Am J Physiol Cell Physiol* 280, C1358-66. (2001).
10. Healy, A. M., Morgenthau, L., Zhu, X., Farber, H. W. & Cardoso, W. V. VEGF is deposited in the subepithelial matrix at the leading edge of branching airways and stimulates neovascularization in the murine embryonic lung. *Dev Dyn* 219, 341-52. (2000).
11. Klekamp, J. G., Jarzecka, K. & Perkett, E. A. Exposure to hyperoxia decreases the expression of vascular endothelial growth factor and its receptors in adult rat lungs. *Am J Pathol* 154, 823-31 (1999).
12. Kaner, R. J. & Crystal, R. G. Compartmentalization of vascular endothelial growth factor to the epithelial surface of the human lung. *Mol Med* 7, 240-6. (2001).
13. Lassus, P. et al. Pulmonary vascular endothelial growth factor and Flt-1 in fetuses, in acute and chronic lung disease, and in persistent pulmonary hypertension of the newborn. *Am J Respir Crit Care Med* 164, 1981-7. (2001).
14. Bhatt, A. J. et al. Disrupted pulmonary vasculature and decreased vascular endothelial growth factor, Flt-1, and TIE-2 in human infants dying with bronchopulmonary dysplasia. *Am J Respir Crit Care Med* 164, 1971-80. (2001).
15. Lassus, P., Ristim#ki, A., Ylikorkala, O., Viinikka, L. & Andersson, S. Vascular Endothelial Growth Factor in Human Preterm Lung. *Am J Respir Crit Care Med* 159, 1429-1433 (1999).
16. Crouch, E. & Wright, J. R. Surfactant proteins a and d and pulmonary host defense. *Annu Rev Physiol* 63, 521-54 (2001).
17. Brown, K. R., England, K. M., Goss, K. L., Snyder, J. M. & Acarregui, M. J. VEGF induces airway epithelial cell proliferation in human fetal lung in vitro. *Am J Physiol Lung Cell Mol Physiol* 281, L1001-10. (2001).
18. Kasahara, Y. et al. Inhibition of VEGF receptors causes lung cell apoptosis and emphysema. *J Clin Invest* 106, 1311-9. (2000).
19. Taraseviciene-Stewart, L. et al. Inhibition of the VEGF receptor 2 combined with chronic hypoxia causes cell death-dependent pulmonary endothelial cell proliferation and severe pulmonary hypertension. *Faseb J* 15, 427-38. (2001).
20. Tian, H., McKnight, S. L. & Russell, D. W. Endothelial PAS domain protein 1 (EPAS1), a transcription factor selectively expressed in endothelial cells. *Genes Dev* 11, 72-82 (1997).
21. Ema, M. et al. A novel bHLH-PAS factor with close sequence similarity to hypoxia-inducible factor 1 alpha regulates VEGF expression and is potentially involved in lung and vascular development. *Proc Natl Acad Sci USA* 94, 4273-4278 (1997).
22. Flamme, I. et al. HRF, a putative basic helix-loop-helix-PAS-domain transcription factor is closely related to hypoxia-inducible factor-1alpha and developmentally expressed in blood vessels. *Mech Development* 63, 51-63 (1997).
23. Tian, H., Hammer, R. E., Matsumoto, A. M., Russell, D. W. & McKnight, S. L. The hypoxia-responsive transcription factor EPAS1 is essential for catecholamine homeostasis and protection against heart failure during embryonic development. *Genes Dev* 12, 3320-4 (1998).
24. Peng, J., Zhang, L., Drysdale, L. & Fong, G. H. The transcription factor EPAS-1/hypoxia-inducible factor 2alpha plays an important role in vascular remodeling. *Proc Natl Acad Sci USA* 97, 8386-91. (2000).
25. Brusselmans, K. et al. Hypoxia-inducible Factor-2alpha (HIF-2alpha) Is Involved in the Apoptotic Response to Hypoglycemia but Not to Hypoxia. *J Biol Chem* 276, 39192-39196. (2001).
26. Botas, C. et al. Altered surfactant homeostasis and alveolar type II cell morphology in mice lacking surfactant protein D. *Proc Natl Acad Sci USA* 95, 11869-74. (1998).
27. Schachtner, S. K., Wang, Y. & Scott Baldwin, H. Qualitative and quantitative analysis of embryonic pulmonary vessel formation. *Am J Respir Cell Mol Biol* 22, 157-65 (2000).
28. Carmeliet, P. et al. Impaired myocardial angiogenesis and ischemic cardiomyopathy in mice lacking the vascular endothelial growth factor isoforms VEGF164 and VEGF188. *Nat Med* 5, 495-502. (1999).
29. Stalmans, I. et al. Arteriolar and venular patterning in retinas of mice selectively expressing VEGF isoforms. *J Clin Invest* 109, 327-36. (2002).
30. Carmeliet, P. et al. Synergism between vascular endothelial growth factor and placental growth factor contributes to angiogenesis and plasma extravasation in pathological conditions. *Nat Med* 7, 575-83. (2001).
31. Oosthuyse, B. et al. Deletion of the hypoxia-response element in the vascular endothelial growth factor promoter causes motor neuron degeneration. *Nat Genet* 28, 131-8. (2001).

32. Champagnat, J. & Fortin, G. Primordial respiratory-like rhythm generation in the vertebrate embryo. *Trends Neurosci* 20, 119-24. (1997).
33. Kaner, R. J. et al. Lung overexpression of the vascular endothelial growth factor gene induces pulmonary edema. *Am J Respir Cell Mol Biol* 22, 657-64. (2000).
34. Rannels, S. R. Impaired surfactant synthesis in fetal type II lung cells from gsd/gsd rats. *Exp Lung Res* 22, 213-29. (1996).
35. Rayani, H. H., Gewolb, I. H. & Floros, J. Glucose decreases steady state mRNA content of hydrophobic surfactant proteins B and C in fetal rat lung explants. *Exp Lung Res* 25, 69-79. (1999).
36. Gilden, C., Sevanian, A., Tierney, D. F., Kaplan, S. A. & Barrett, C. T. Regulation of fetal lung phosphatidyl choline synthesis by cortisol: role of glycogen and glucose. *Pediatr Res* 11, 845-8. (1977).
37. Ren, J. M., Gulve, E. A., Cartee, G. D. & Holloszy, J. O. Hypoxia causes glycogenolysis without an increase in percent phosphorylase a in rat skeletal muscle. *Am J Physiol* 263, E1086-91. (1992).
38. Zhong, H. et al. Modulation of hypoxia-inducible factor 1alpha expression by the epidermal growth factor/phosphatidylinositol 3-kinase/PTEN/AKT/FRAP pathway in human prostate cancer cells: implications for tumor angiogenesis and therapeutics. *Cancer Res* 60, 1541-5 (2000).
39. Akeno, N., Robins, J., Zhang, M., Czyzyk-Krzeska, M. F. & Clemens, T. L. Induction of Vascular Endothelial Growth Factor by IGF-I in Osteoblast-Like Cells Is Mediated by the PI3K Signaling Pathway through the Hypoxia-Inducible Factor-2alpha. *Endocrinology* 143, 420-5. (2002).
40. Jiang, B. H. et al. Phosphatidylinositol 3-kinase signaling controls levels of hypoxia-inducible factor 1. *Cell Growth Differ* 12, 363-9. (2001).
41. Bhatt, A. J., Amin, S. B., Chess, P. R., Watkins, R. H. & Maniscalco, W. M. Expression of vascular endothelial growth factor and Flk-1 in developing and glucocorticoid-treated mouse lung. *Pediatr Res* 47, 606-13. (2000).
42. Braun, L., Kardon, T., Reisz-Porszasz, Z. S., Banhegyi, G. & Mandl, J. The regulation of the induction of vascular endothelial growth factor at the onset of diabetes in spontaneously diabetic rats. *Life Sci* 69, 2533-42. (2001).
43. Yi, M., Tong, G. X., Murry, B. & Mendelson, C. R. Role of CBP/p300 and SRC-1 in Transcriptional Regulation of the Pulmonary Surfactant Protein-A (SP-A) Gene by Thyroid Transcription Factor-1 (TTF-1). *J Biol Chem* 277, 2997-3005. (2002).
44. Matsui, R., Brody, J. S. & Yu, Q. FGF-2 induces surfactant protein gene expression in foetal rat lung epithelial cells through a MAPK-independent pathway. *Cell Signal* 11, 221-8 (1999).
45. Bernatchez, P. N., Winstead, M. V., Dennis, E. A. & Sirois, M. G. VEGF stimulation of endothelial cell PAF synthesis is mediated by group V 14 kDa secretory phospholipase A2. *Br J Pharmacol* 134, 197-205. (2001).
46. Bourbon, J. R., Hoffman, D. R. & Johnston, J. M. Effect of platelet-activating factor on glycogen metabolism in fetal rat lung. *Exp Lung Res* 17, 789-801. (1991).
47. Rooney, S. A. Regulation of surfactant secretion. *Comp Biochem Physiol A Mol Integr Physiol* 129, 233-43. (2001).
48. Pugazhenthi, S. & Khandelwal, R. L. Regulation of glycogen synthase activation in isolated hepatocytes. *Mol Cell Biochem* 149-150, 95-101. (1995).
49. Ng, Y. S., Rohan, R., Sunday, M. E., Demello, D. E. & D'Amore, P. A. Differential expression of VEGF isoforms in mouse during development and in the adult. *Dev Dyn* 220, 112-21. (2001).
50. Corne, J. et al. IL-13 stimulates vascular endothelial cell growth factor and protects against hyperoxic acute lung injury. *J Clin Invest* 106, 783-91. (2000).
51. Shweiki, D., Itin, A., Soffer, D. & Keshet, E. Vascular endothelial growth factor induced by hypoxia may mediate hypoxia-initiated angiogenesis. *Nature* 359, 843-5. (1992).
52. Van Veldhoven, P. P. & Bell, R. M. Effect of harvesting methods, growth conditions and growth phase on diacylglycerol levels in cultured human adherent cells. *Biochim Biophys Acta* 959, 185-96. (1988).
53. Van Veldhoven, P. P. & Mannaerts, G. P. Inorganic and organic phosphate measurements in the nanomolar range. *Anal Biochem* 161, 45-8. (1987).
54. Kaluzny, M. A., Duncan, L. A., Merritt, M. V. & Epps, D. E. Rapid separation of lipid classes in high yield and purity using bonded phase columns. *J Lipid Res* 26, 135-40. (1985).
55. Keller, B. B., MacLennan, M. J., Tinney, J. P. & Yoshigi, M. In vivo assessment of embryonic cardiovascular dimensions and function in day-10.5 to -14.5 mouse embryos. *Circ Res* 79, 247-55. (1996).
56. Hoet, P. H., Gilissen, L. & Nemery, B. Polyanions protect against the in vitro pulmonary toxicity of polycationic paint components associated with the Ardystil syndrome. *Toxicol Appl Pharmacol* 175, 184-90. (2001).

What is claimed is:

1. A method to treat neonatal respiratory distress syndrome which comprises administering a therapeutically effective amount of vascular endothelial growth factor (VEGF), or a pharmaceutically acceptable salt of VEGF to a fetus or neonate in need of treatment.

2. The method of claim 1, wherein VEGF is selected from the group consisting of $VEGF_{120}$, $VEGF_{188}$ and $VEGF_{165}$.

3. The method of claim 1, wherein the VEGF is $VEGF_{165}$.

4. The method of claim 1, wherein administration is intra-uterine or intra-amniotically to a fetus.

5. The method of claim 1, wherein administration is intra-tracheal.

* * * * *

UNITED STATES PATENT AND TRADEMARK OFFICE
CERTIFICATE OF CORRECTION

PATENT NO. : 7,307,060 B2  
APPLICATION NO. : 11/226771  
DATED : December 11, 2007  
INVENTOR(S) : Compernolle et al.

It is certified that error appears in the above-identified patent and that said Letters Patent is hereby corrected as shown below:

Column 3, Line 42, "that the respons to" should be changed to --that the response to--

Column 5, Line 12, "Fab, F(ab)'$_2$ and" should be changed to --F(ab), F(ab)'$_2$ and--

Column 7, Line 26, "on Sep. 09, 1984." should be changed to --on Sep. 13, 1984.--

Column 7, Line 30, "HIF-2α a nd" should be changed to --HIF-2α and--

Column 7, Line 63, "Small molecules, eg small" should be changed to --Small molecules, e.g., small--

Column 9, Lines 10-11, "venticular septal defect" should be changed to --ventricular septal defect--

Column 13, Line 54, "(N: 20% O2) or hypoxia (H: 10% O2) for" should be changed to --(N: 20% $O_2$) or hypoxia (H: 10% $O_2$) for--

Column 16, Line 13-14, "(N: 20% O2) or after hypoxic exposure (H: 10% O2)" should be changed to --(N: 20% $O_2$) or after hypoxic exposure (H: 10% $O_2$)--

Column 18, After Line 67, insert the following as Table 10.

--

| % airsurface/(tissue+air)surface P0 | | | | | | |
|---|---|---|---|---|---|---|
| genotype | Wild type (n=3) | HIF-2α-/- (n=3) | VEGF 120 isoform (n=3) | PLKO-/- (n=3) | VEGF 164 (n=2) | VEGF188 (n=2) |
| Mean | 57.3% | 29.0% | 23.3% | 48.5% | 64.7% | 57.6% |
| SEM | 1.8% | 2.8% | 4.26% | 4.3% | 2.9% | 2.5% |
| p-value in comparence with wild type | | 0.00108 | 0.00185 | 0.0721 | 0.11 | 0.91 |

--

UNITED STATES PATENT AND TRADEMARK OFFICE
CERTIFICATE OF CORRECTION

PATENT NO. : 7,307,060 B2
APPLICATION NO. : 11/226771
DATED : December 11, 2007
INVENTOR(S) : Compernolle et al.

It is certified that error appears in the above-identified patent and that said Letters Patent is hereby corrected as shown below:

Column 20, Line 12, "in the HIF-2α-/-." should be changed to --in the HIF-2α$^{-/-}$.--

Column 20, Line 12, "septa are to thick" should be changed to --septa are too thick--

Column 20, Line 15, "in the HIF-2α-/-." should be changed to --in the HIF-2α$^{-/-}$.--

Column 21, Line 8, "cell actin staining)" should be changed to --cell actin staining).--

Column 21, Line 64, "wt and HIF-2α-/-." should be changed to --wt and HIF-2α$^{-/-}$.--

Column 22, Line 5, "well as HIF-2α-/-" should be changed to --well as HIF-2α$^{-/-}$--

Column 22, Line 24, "a downsteam target" should be changed to --a downstream target--

Column 24, Line 15, "PDGFis not" should be changed to --PDGF is not--

Column 26, Line 36, "anti-Flk1 antibodies" should be changed to --anti-Flk-1 antibodies--

Columns 27-28, Line 20, "mature E17.5 fetues" should be changed to --mature E17.5 fetuses--

Column 29, Line 56, "and HIF-2α-/- ES" should be changed to -- and HIF-2α$^{-/-}$ ES--

Column 29, Line 62, "and 6 mM MgCl2." should be changed to --and 6 mM MgCl$_2$.--

Column 29, Line 63, "H2O and transcribed" should be changed to --H$_2$O and transcribed--

Column 30, Line 16, "CompleteTM was" should be changed to --Complete$^{TM}$ was--

UNITED STATES PATENT AND TRADEMARK OFFICE
CERTIFICATE OF CORRECTION

PATENT NO. : 7,307,060 B2
APPLICATION NO. : 11/226771
DATED : December 11, 2007
INVENTOR(S) : Compernolle et al.

It is certified that error appears in the above-identified patent and that said Letters Patent is hereby corrected as shown below:

Column 30, Line 20, "of Cu2+ to Cu1+ in" should be changed to --of $Cu^{2+}$ to $Cu^{1+}$ in--

Column 30, Line 22, "between Cu1+ and" should be changed to --between $Cu^{1+}$ and--

Column 32, Line 54, "were perfomed in utero" should be changed to --were performed in utero--

Column 33, Line 60, "factor, Fit-1, and" should be changed to --factor, Flt-1, and--

Signed and Sealed this

Seventeenth Day of June, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: primer A

<400> SEQUENCE: 1
acggaactcc aggtcccttg tcgctgc					27

```
<210> SEQ ID NO 2
<211> LENGTH: 27
<212> TYPE: DNA
<213> ORGANISM: Artificial Sequence
<220> FEATURE:
<223> OTHER INFORMATION: primer B

<400> SEQUENCE: 2
acaggagctt atgtgtccga aggaagc                                27

<210> SEQ ID NO 3
<211> LENGTH: 27
<212> TYPE: DNA
<213> ORGANISM: Artificial Sequence
<220> FEATURE:
<223> OTHER INFORMATION: primer hprt190

<400> SEQUENCE: 3
gtcgccctct gtgtgctcaa gggggc                                 27

<210> SEQ ID NO 4
<211> LENGTH: 27
<212> TYPE: DNA
<213> ORGANISM: Artificial Sequence
<220> FEATURE:
<223> OTHER INFORMATION: primer hprt563

<400> SEQUENCE: 4
aaacttgtct ggaatttcaa atccaac                                27

<210> SEQ ID NO 5
<211> LENGTH: 11
<212> TYPE: PRT
<213> ORGANISM: Artificial Sequence
<220> FEATURE:
<223> OTHER INFORMATION: PR-11

<400> SEQUENCE: 5

Arg Arg Arg Pro Arg Pro Pro Tyr Leu Pro Ala
 1               5                  10
```